(12) United States Patent
Hsueh et al.

(10) Patent No.: US 6,224,961 B1
(45) Date of Patent: May 1, 2001

(54) ABSORBENT MACROSTRUCTURE MADE FROM MIXTURES OF DIFFERENT HYDROGEL-FORMING ABSORBENT POLYMERS FOR IMPROVED FLUID HANDLING CAPABILITY

(75) Inventors: Kesyin F. Hsueh; Reiko Sasaki, both of Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/230,906

(22) PCT Filed: Aug. 1, 1997

(86) PCT No.: PCT/US97/12854

§ 371 Date: Mar. 1, 1999

§ 102(e) Date: Mar. 1, 1999

(87) PCT Pub. No.: WO98/06364

PCT Pub. Date: Feb. 19, 1998

(51) Int. Cl.$^7$ ............... A61F 13/15; B32B 3/26

(52) U.S. Cl. ............ 428/72; 428/220; 428/313.5; 428/317.9; 521/919; 604/368

(58) Field of Search ............ 428/72, 220, 313.5, 428/317.9; 521/919; 604/368

(56) References Cited

U.S. PATENT DOCUMENTS

| | | | |
|---|---|---|---|
| Re. 32,649 | 4/1988 | Brandt et al. | 604/368 |
| 3,669,103 | 6/1972 | Harper et al. | 128/156 |
| 3,670,731 | 6/1972 | Harmon | 128/284 |
| 4,340,706 | 7/1982 | Obaysashi et al. | 526/207 |
| 4,506,062 | 3/1985 | Flesher et al. | 526/211 |
| 4,654,039 | 3/1987 | Brandt et al. | 604/368 |
| 4,673,402 | 6/1987 | Weisman et al. | 604/368 |
| 4,735,987 | 4/1988 | Morita et al. | 524/436 |
| 4,834,735 | 5/1989 | Alemany et al. | 604/368 |
| 4,935,022 | 6/1990 | Lash et al. | 604/368 |
| 5,102,597 | 4/1992 | Roe et al. | 264/126 |
| 5,124,188 | 6/1992 | Roe et al. | 428/72 |
| 5,149,334 | 9/1992 | Lahrman et al. | 604/367 |
| 5,324,561 | 6/1994 | Rezai et al. | 428/72 |

*Primary Examiner*—Blaine Copenheaver
(74) *Attorney, Agent, or Firm*—T. David Reed; Edward J. Milbrada; Caroline Wei-Berk

(57) ABSTRACT

Porous, absorbent macrostructures having improved fluid handling capabilities that include inter-particle bonded aggregates, and are useful in absorbent articles, such as diapers, adult incontinence pads and sanitary napkins, are disclosed. The inter-particle bonded aggregates of these macrostructures are made from mixtures of particulate absorbent polymers having different fluid handling properties, different shapes, or both. These macrostructures can be made from a wider variety of hydrogel-forming absorbent polymers without sacrificing desired fluid handling properties, and without being prone to gel blocking.

10 Claims, 4 Drawing Sheets

ABSORBENT MACROSTRUCTURE MADE FROM MIXTURES OF DIFFERENT HYDROGEL-FORMING ABSORBENT POLYMERS FOR IMPROVED FLUID HANDLING CAPABILITY

TECHNICAL FIELD

This application relates to porous, absorbent macrostructures that comprise flexible interparticle bonded aggregates. This application particularly relates to porous absorbent macrostructures where the interparticle bonded aggregates are made from mixtures of particulate absorbent polymers having different fluid handling properties, or shapes, or both, that impart improved fluid handling capability to the macrostructure.

BACKGROUND

The development of highly absorbent members for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain absorbent polymers often referred to as "hydrogels," "superabsorbents" or "hydrocolloid" material has been particularly important. See, for example, U.S. Pat. No. 3,699,103 (Harper et al), issued Jun. 13, 1972, and U.S. Pat. No. 3,770,731 (Harnon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers.

Prior to the use of these hydrogel-forming absorbent polymers, it was general practice to form absorbent structures, such as those suitable for use in infant diapers, entirely from wood pulp fluff. Given the relatively low amount of fluid absorbed by wood pulp fluff on a gram of fluid absorbed per gram of wood pulp fluff, it was necessary to employ relatively large quantities of wood pulp fluff, thus necessitating the use of relatively bulky, thick absorbent structures. The introduction of these hydrogel-forming absorbent polymers into such structures has allowed the use of less wood pulp fluff. These hydrogel-forming absorbent polymers are superior to fluff in their ability to absorb large volumes of aqueous body fluids, such as urine (i.e., at least about 15 g/g), thus making smaller, thinner absorbent structures feasible.

These hydrogel-forming absorbent polymers are often made by initially polymerizing unsaturated carboxylic acids or derivatives thereof, such as acrylic acid, alkali metal (e.g., sodium and/or potassium) or ammonium salts of acrylic acid, alkyl acrylates, and the like. These polymers are rendered water-insoluble, yet water-swellable, by slightly cross-linking the carboxyl group-containing polymer chains with conventional di- or poly-functional monomer materials, such as N, N'-methylenebisacrylamide, trimethylol propane triacrylate or triallyl amine. These slightly crosslinked absorbent polymers still comprise a multiplicity of anionic (charged) carboxyl groups attached to the polymer backbone. It is these charged carboxy groups that enable the polymer to absorb body fluids as the result of osmotic forces, thus forming hydrogels.

The degree of cross-linking determines not only the water-insolubility of these hydrogel-forming absorbent polymers, but is also an important factor in establishing two other characteristics of these polymers: their absorbent capacity and gel strength. Absorbent capacity or "gel volume" is a measure of the amount of water or body fluid that a given amount of hydrogel-forming polymer will absorb. Gel strength relates to the tendency of the hydrogel formed from these polymers to deform or "flow" under an applied stress. Hydrogel-forming polymers useful as absorbents in absorbent structures and articles such as disposable diapers need to have adequately high gel volume, as well as adequately high gel strength. Gel volume needs to be sufficiently high to enable the hydrogel-forming polymer to absorb significant amounts of the aqueous body fluids encountered during use of the absorbent article. Gel strength needs to be such that the hydrogel formed does not deform and fill to an unacceptable degree the capillary void spaces in the absorbent structure or article, thereby inhibiting the absorbent capacity of the structure/article, as well as the fluid distribution throughout the structure/article. See, for example, U.S. Pat. No. 4,654,039 (Brandt et al), issued Mar. 31, 1987 (reissued Apr. 19, 1988 as U.S. Reissue Pat. No. 32,649) and U.S. Pat. No. 4,834,735 (Alemany et al), issued May 30, 1989.

Prior absorbent structures have generally comprised relatively low amounts (e.g., less than about 50% by weight) of these hydrogel-forming absorbent polymers. See, for example, U.S. Pat. No. 4,834,735 (Alemany et al), issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking, especially when included in the absorbent structure at higher levels. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent member are fully saturated or before the fluid can diffuse or wick past the "blocking" particles into the rest of the absorbent member.

Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et al), issued May 30, 1989. Low gel strength hydrogel-forming absorbent polymers also tend to be those having higher fluid capacities. Gel strength can be increased by surface crosslinking of these higher fluid capacity hydrogel-forming absorbent polymers. Unfortunately, while surface crosslinking increases gel strength, it also tends to lower the fluid capacity of the hydrogel-forming absorbent polymer.

Gel blocking can also occur when the hydrogel-forming absorbent polymer is in the form of regular shaped particles, such as spherically shaped particles. Spherical shaped particles typically result when the hydrogel-forming absorbent polymer is formed by multi-phase polymerization processing techniques such as inverse emulsion polymerization or inverse suspension polymerization procedures. See U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988. Because these spherical shaped particles are prone to gel blocking, multi-phase polymerization processing techniques have been considered less desirable in synthesizing hydrogel-forming absorbent polymers. See U.S. Pat. No. 5,124,188 (Roe et al), issued Jun. 23, 1992.

To improve capillary capability and thus minimize gel blocking, particles of these hydrogel-forming absorbent polymers have been formed into interparticle crosslinked aggregate macrostructures, typically in the form of sheets or strips. These aggregate macrostructures have been prepared by initially mixing the particles of hydrogel-forming absorbent polymer with a solution of a nonionic crosslinking agent such as glycerol, water and a hydrophilic organic solvent such as isopropanol. See U.S. Pat. No. 5,102,597 (Roe et al), issued Apr. 7, 1992; U.S. Pat. No. 5,124,188 (Roe et al), issued Jun. 23, 1992; and U.S. Pat. No. 5,149,344 (Lahrman et al), issued Sep. 22, 1992. See also U.S. Pat. No. 5,324,561 (Rezai et al), issued Jun. 23, 1994, which discloses an improved porous aggregate macrostructure where the particles of hydrogel-forming absorbent polymer are crosslinked with cationic amino-epichlorohydrin adducts, such as KYMENE.

Because the particulate nature of the absorbent polymer is retained, these macrostructures provide pores between adjacent particles that are interconnected such that the macrostructure is fluid permeable (i.e., has capillary transport channels). Due to the interparticle crosslink bonds formed between the particles, the resultant macrostructures also have improved structural integrity, increased fluid acquisition and distribution rates, and minimal gel blocking characteristics. Even so, the fluid handling capability of these macrostructures is still somewhat dependent on the fluid handling capability of the particles of hydrogel-forming absorbent polymer from which they are made. For example, macrostructures made from low gel strength hydrogel-forming absorbent polymers or spherical shaped particles of hydrogel-forming absorbent polymer are still potentially subject to gel blocking. Also, macrostructures made from surface crosslinked hydrogel-forming absorbent polymers still have less than optimum permeability characteristics.

Accordingly, it would be desirable to be able to make absorbent aggregate macrostructures of bonded absorbent particles that: (1) can use hydrogel-forming absorbent polymers made by a variety of methods; (2) are less prone to gel blocking; (3) have optimum permeability characteristics; and/or (4) provide an improved combination of fluid handling capabilities.

SUMMARY

The present invention relates to porous, absorbent, macrostructures having improved fluid handling capabilities that comprise interparticle bonded aggregates. These aggregates comprise a multiplicity of interconnected crosslinked particles comprising substantially water-insoluble, absorbent, hydrogel-forming polymer material. The hydrogel-forming polymer material comprises a mixture selected of (a) mixtures of from about 50 to about 95% of a first hydrogel-forming polymer having a Saline Flow Conductivity (SFC) value of at least about $5 \times 10^{-7}$ $cm^3 sec/g$ and a Performance under Pressure (PUP) capacity value of at least about 23 g/g under a confining pressure of 0.7 psi (5 kPa) and from about 5 to about 50% of a second hydrogel-forming polymer having an Absorptive Capacity value of at least about 25 g/g; (b) mixtures of from about 20 to about 40% of a first hydrogel-forming polymer in the form of spherical shaped particles and from about 60 to about 80% of a second hydrogel-forming polymer in the form of nonspherical shaped particles; and (c) combinations of (a) and (b). The interparticle bonded aggregate comprises pores between adjacent particles. The pores are interconnected by intercommunicating channels so as to form a liquid permeable macrostructure. The circumscribed dry volume of the macrostructure is greater than about 0.008 $mm^3$.

The porous, absorbent macrostructures according to the present invention are useful, alone, or in combination with other absorbent materials, in absorbent structures for various absorbent articles, including diapers, adult incontinence pads, sanitary napkins, and the like. These porous absorbent macrostructures provide a particularly desirable combination of fluid handling properties including relatively high fluid permeability and relatively high fluid capacity. The macrostructures of the present invention can also be made from a wider variety of hydrogel-forming absorbent polymers without sacrificing these desired fluid handling properties and without being prone to gel blocking. Indeed, the ability to use greater quantities of spherical shaped particles of hydrogel-forming absorbent polymers provides processing advantages such as a more uniform flow rate during the making of these macrostructures.

DETAILED DESCRIPTION

Definitions

Figure 1:
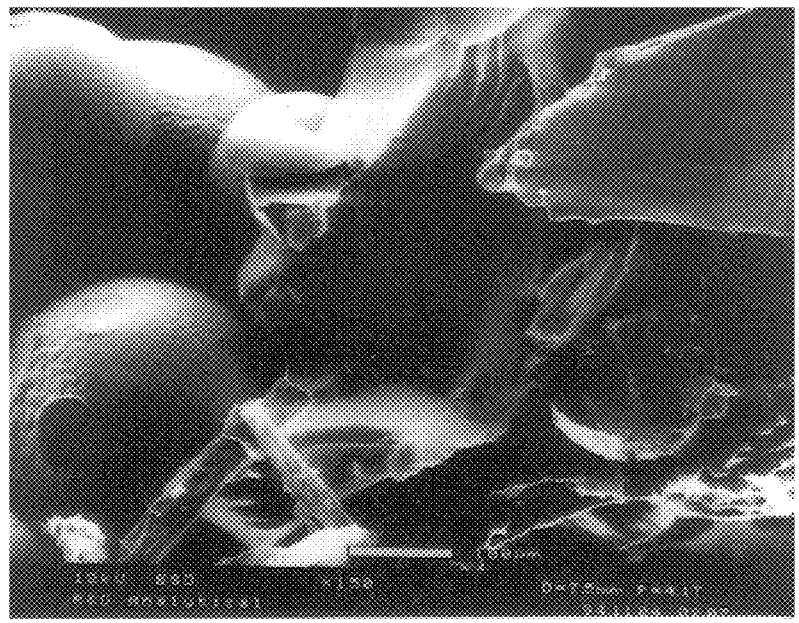
FIG. 1 is a scanning electron microscope photograph of a typical macrostructure of the present invention. The macrostructure shown is fabricated with the use of irregular shaped and spherical shaped superabsorbent polymers.
Figure 2:
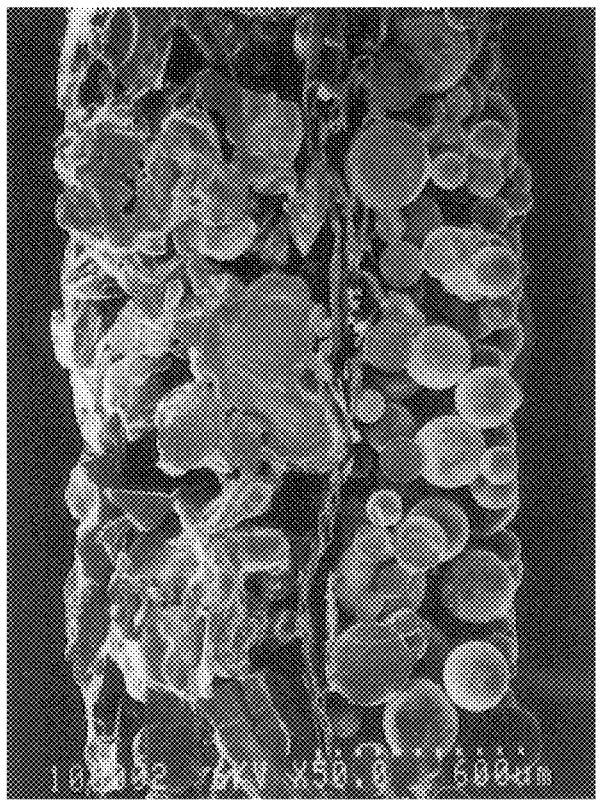
FIG. 2 is a scanning electron microscope photograph of a macrostructure of the present invention. The structure is fabricated by attaching one irregular shaped superabsorbent polymer on one side of a fiber web, and a spherical shaped polymer on the other side.

"Body fluids" includes urine, menses and vaginal discharges.

"Comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

I. Porous Absorbent Macrostructures
A. General Characteristics

Porous, absorbent macrostructures according to the present invention are structures capable of absorbing large quantities of liquids such as water and/or body exudates (e.g., urine or menses) and then retaining such liquids under moderate pressures. Because of the particulate nature of the precursor particles, the macrostructure has pores between adjacent precursor particles. These pores are interconnected by intercommunicating channels such that the macrostructure is liquid permeable (i.e., has capillary transport channels).

Due to the bonds formed between the precursor particles, the resultant aggregate macrostructure has improved structural integrity, increased liquid acquisition and distribution rates, and minimal gel-blocking characteristics. It has been found that when the macrostructure is contacted with liquids, the macrostructure swells generally isotropically even under moderate confining pressures, absorbs such liquids into the pores between the precursor particles, and then imbibes such liquids into the particles. The isotropic swelling of the macrostructure allows the precursor particles and the pores to maintain their relative geometry and spatial relationships even when swollen. Thus, the macrostructures are relatively "fluid stable" in that the precursor particles do not dissociate from each other, thereby minimizing the incidence of gel blocking and allowing the capillary channels to be maintained and enlarged when swollen so that the macrostructure can acquire and transport subsequent loadings of liquid, even excess liquid.

"Macrostructure" means a structure having a circumscribed volume when substantially dry (i.e., circumscribed dry volume) of at least about 0.008 $mm^3$, preferably at least about 10.0 $mm^3$, more preferably at least about 100 $mm^3$, more preferably at least about 500 $mm^3$. Typically, the macrostructures of the present invention will have a circumscribed dry volume much greater than about 500 $mm^3$. In preferred embodiments of the present invention, the macrostructures have a circumscribed dry volume of between about 1000 $mm^3$ and about 100,000 $mm^3$.

While the macrostructures of the present invention can have a number of shapes and sizes, they are typically in the form of sheets, films, cylinders, blocks, spheres, fibers, filaments, or other shaped elements. The macrostructures will generally have a thickness or diameter between about 0.2 mm and about 10.0 mm. Preferably for use in absorbent products, the macrostructures are in the form of a sheet. The term "sheet" describes macrostructures having a thickness of at least about 0.2 mm. The sheets will preferably have a thickness between about 0.5 mm and about 10 mm, typically from about 1 mm to about 3 mm.

The porous, absorbent macrostructures of the present invention comprise interparticle bonded aggregates. These interparticle bonded aggregates usually comprise about 8 or more previously independent precursor particles. For preferred circumscribed dry volumes and sizes of the individual precursor particles used herein, these interparticle bonded aggregates typically are formed from about 100,000 or more individual precursor particles. These individual precursor particles can comprise granules, pulverulents, spheres, flakes, fibers, aggregates or agglomerates. The individual precursor particles can have a variety of shapes, such as cubic, rod-like, polyhedral, spherical, rounded, angular, irregular, randomly-sized irregular shapes, e.g., pulverulent products of grinding or pulverizing steps, or shapes having a large greatest dimension/smallest dimension ratio so as to be needle-like, flake-like, or fiber-like.

The interparticle bonded aggregate comprising the macrostructures of the present invention are formed, in essence, by the joining or adhering together of adjacent particles. The adhesive agent is essentially the polymeric material that is present in the surface of these particles. When these precursor particles are treated with a crosslinking agent and physically associated, the polymer material present in the surface of these particles is sufficiently plastic and cohesive (e.g., sticky) such that adjacent particles are adhered together, typically as discrete linking portions between the particles. The crosslinking reaction between the particles then sets this adhered structure such that the particles in the aggregate remain cohesively bonded together.

B. Precursor Absorbent Particles

The macrostructures of the present invention are formed from precursor particles that comprise substantially water-insoluble polymer materials capable of absorbing large quantities of liquids. Such polymer materials are referred to hereafter as "hydrogel-forming absorbent polymers." Since the macrostructures of the present invention comprise interparticle bonded aggregates, these hydrogel-forming absorbent polymer materials will be discussed herein with respect to those forming the precursor particles.

Although the precursor particles can have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. For purposes of this invention, the mass average particle size of the precursor particles is important in determining the characteristics and properties of the resultant macrostructures. The mass average particle size of a given sample of precursor particles is defined as the particle size which is the average particle size of the sample on a mass basis. A method for determining the mass average particle size of a sample is described in the Test Methods section of U.S. Pat. No. 5,324,561 (Rezai et al), issued Jun. 23, 1994. The mass average particle size of the precursor particles will generally be from about 20 microns to about 1500 microns, more preferably from about 50 microns to about 1000 microns. In preferred embodiments of the present invention, the precursor particles have a mass average particle size less than about 1000 microns, more preferably less than about 600 microns, more preferably less than about 500 microns.

The particle size of materials having a large greatest dimension/smallest dimension, such as fibers, is typically defined by their largest dimension. For example, if absorbent, polymeric fibers (i.e. superabsorbent fibers) are used in the macrostructures of the present invention, the length of the fibers is used to define the "particle size." (The denier and/or the diameter of the fibers can also be specified.) In exemplary embodiments of the present invention, the fibers have a length greater than about 5 mm, preferably between about 10 mm and about 100 mm, more preferably between about 10 mm and about 50 mm.

The hydrogel-forming absorbent polymer material that comprise these precursor particles have a multiplicity of anionic, functional groups, such as sulfonic acid, and more typically carboxy, groups. Examples of polymer materials suitable for use as the precursor particles herein include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof. See U.S. Pat. No. 5,324,561 (Rezai et al), issued Jun. 23, 1994, which generally describes suitable monomers for the preparation of hydrogel-forming absorbent polymers.

Preferred polymer materials for use in the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. See, for example, U.S. Pat. No. 4,093,776 (Aoki et al), issued Jun. 6, 1978, U.S. Pat. No. 4,666,983 (Tsubakimoto et al), issued May 19, 1987, and U.S. Pat. No. 4,734,478 (Tsubakimoto et al), issued Mar. 29, 1988 where representative examples of these types of hydrogel-forming absorbent polymer are disclosed.

More preferred polymer materials for use in making the precursor particles are slightly network crosslinked polymers of partially neutralized polyacrylic acids and starch derivatives thereof. Preferably, the precursor particles comprise from about 50 to about 95%, preferably about 75%, neutralized, slightly network crosslinked, polyacrylic acid (i.e. poly (sodium acrylate/acrylic acid)). Processes for network crosslinking the polymers and typical network crosslinking agents are described in greater detail in U.S. Pat. No. 4,076,663, supra.

The individual precursor particles can be formed in any conventional manner. For example, precursor particles can be prepared by methods that involve aqueous solution or other solution polymerization methods. See, for example, U.S. Reissue Pat. No. 32,649 (Brandt et al), reissued Apr. 19, 1988. Precursor particles useful in the present invention can also be manufactured using multi-phase polymerization processing techniques such as inverse-emulsion polymerization or inverse suspension polymerization procedures. See, for example, U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, for processes involving inverse suspension polymerization. As will be discussed hereafter, the particular process used in making these precursor particles can be important in determining their fluid permeability and capacity properties, as well as the shape of the resultant particles.

While all of the precursor particles are preferably formed from the same polymer material with the same properties, this need not be the case. For example, some precursor particles can comprise a starch-acrylic acid graft copolymer while other precursor particles can comprise a slightly network crosslinked polymer of partially neutralized polyacrylic acid. Further, the precursor particles can vary in size, shape, absorptive capacity, or any other property or characteristic. In a preferred embodiment of the present invention, the precursor particles consist essentially of slightly network crosslinked polymers of partially neutralized polyacrylic acid, each precursor particle having similar properties.

In preferred embodiments of the present invention, the precursor particles used to form the bonded particle aggregates are substantially dry. "Substantially dry" means that the precursor particles have a liquid content, typically water or other solution content, less than about 50%, preferably less than about 20%, more preferably less than about 10%, by weight of the precursor particles. In general, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer material can then be chopped or pulverized to form substantially dry precursor particles of substantially water-insoluble, absorbent, hydrogel-forming, polymer material.

C. Mixtures of Precursor Particles Providing Improved Fluid Handling Properties

The key aspect of the present invention is using mixtures of precursor particles that have: (1) different fluid handling properties; (2) different shapes; or (3) both. It has been found that mixtures of precursor particles having different fluid handling properties, shapes or both can impart improved overall fluid handling capability to the resultant macrostructure. This is typically manifested as a combination higher fluid permeability/performance and higher fluid capacity in the resultant macrostructures made from these mixtures. Indeed, macrostructures made from mixtures of precursor particles according to present invention minimize the potential problem of "gel blocking" without sacrificing desired fluid capacity.

Mixtures according to variant (1) of the present invention comprise precursor particles made from: (a) a first hydrogel-forming polymer having a relatively high Saline Flow Conductivity (SFC) value and relatively high Performance Under Pressure (PUP) capacity (for higher gel permeability/performance); and (b) a second hydrogel-forming polymer having a relatively high Absorptive Capacity. Generally, these mixtures comprise from about 50 to about 95% of the higher gel permeability/performance hydrogel-forming polymer and from about 5 to about 50% the higher fluid capacity hydrogel-forming polymer. Preferably, these mixtures comprise from about 60 to about 95% of the higher gel permeability/performance hydrogel-forming polymer and from about 5 to about 40% of the higher fluid capacity hydrogel-forming polymer, and more preferably from about 60 to about 80% of the higher gel permeability/performance hydrogel-forming polymer and from about 20 to about 40% of the higher fluid capacity hydrogel-forming polymer.

Precursor particles useful in the present invention that have relatively high Saline Flow Conductivity (SFC) values and relatively high Performance Under Pressure (PUP) capacity are disclosed in copending U.S. application Ser. No. 219,574 (Goldman et al), filed Mar. 29, 1994. These high gel layer permeability/performance precursor particles have SFC values of at least about $5 \times 10^{-7}$ cm$^3$sec/g, preferably at least about $10 \times 10^{-7}$ cm$^3$sec/g, and more preferably at least about $100 \times 10^{-7}$ cm$^3$sec/g. Typically, these SFC values are in the range of from about 30 to about $1000 \times 10^{-7}$ cm$^3$ sec/g, more typically from about 50 to about $500 \times 10^{-7}$ cm$^3$ sec/g, and more typically from about 100 to about $350 \times 10^{-7}$ cm$^3$ sec/g. These high gel layer permeability/performance precursor particles also generally have a PUP capacity at least about 23 g/g, preferably at least about 25 g/g, and more preferably at least about 29 g/g. Typically, these PUP capacity values are in the range of from about 23 to about 35 g/g, more typically from about 25 to about 33 g/g, more typically from about 29 to about 33 g/g.

The preferred processes for obtaining precursor particles having relatively high SFC and PUP capacity values involve surface crosslinking of the initially formed polymers. A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hidrogel-forming absorbent polymer either during or after the primary polymerization process such as to generate a higher level of crosslinking at or near the surface (e.g., heating to induce the formation of anhydride and/or ester crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.) See copending U.S. application Ser. No. 219,574 (Goldman et al), filed Mar. 29, 1994.

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90108789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992. See also copending U.S. application Ser. No. 219,574 (Goldman et al), filed Mar. 29, 1994, especially Examples 1 to 4. Suitable hydrogel-forming absorbent polymers having relatively high SFC and PUP capacity values include L76If made by Nippon Shokubai, SXP made by Chemische Fabrik Stockhausen, XZ made by Dow Chemical and XP-30 made by Nalco Chemical.

Precursor particles useful in the present invention that have a relatively high Absorptive Capacity and a relatively high Absorption (AAP) value are disclosed in the U.S. Pat. No. 4,076,663 (Matsuda et al), issued Feb. 28, 178, U.S. Reissue Pat. No. 32,649 (Brandt et al), reissued Apr. 19, 1988, U.S. Pat. No. 4,625,001 (Tsubakimoto et al), issued Nov. 25, 1986, U.S. Pat. No. 4,666,983 (Tsubakimoto et al), issued May 19, 1987, U.S. Pat. No. 4,734,478 (Tsubakimoto et al), issued Mar. 29, 1988, U.S. Pat. No. 4,735,987 (Morita et al), issued Apr. 5, 1988, U.S. Pat. No. 4,973,632 (Nagasuna et al), issued Nov. 27, 1990, U.S. Pat. No. 5,264,471 (Chmelir), issued Nov. 23, 1993 and European Pat. No. Application 530,438 (Chambers et al), published Mar. 10, 1993, all of which are. "Absorptive Capacity" refers to the capacity of a given polymer material to absorb fluids with which it comes into contact and can vary significantly with the nature of the fluid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material. See Test Methods section hereafter. The AAP value is reflective of the demand absorbency of the hydrogel-forming polymer, i.e. the absorptive capacity of the polymer when subjected to an external pressure of 0.3 psi. See Test Methods section hereafter.

These higher fluid capacity precursor particles have Absorptive Capacity values of at least about 25 grams, more preferably at least about 35 grams, more preferably at least about 45 grams, of Synthetic Urine per gram of polymer. Typically, these higher fluid capacity precursor particles have an Absorptive Capacity value of from about 25 to about 70 grams, more typically from about 40 to about 60 grams of Synthetic Urine per gram of polymer material.

The preferred processes for obtaining these precursor particles having relatively high Absorptive Capacity value involve aqueous solution or other solution polymerization methods. As described in the above-referenced U.S. Pat. Reissue No. 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. Suitable hydrogel-forming absorbent polymers having relatively high Absorptive Capacity and AAP values include, but are not limited to, IM 1000 made by Hoechst Celanese, L74 made by Nippon Shokubai and F201 made by Nippon Gohsei.

Mixtures according to variant (2) of the present invention comprise precursor particles made from: (a) a first hydrogel-forming polymer in the form of spherical shaped particles which can include spherical shaped agglomerates of the first hydrogel-forming polymer (typically produced by a suspension polymerization process); and (b) a second hydrogel-forming polymer in the form of nonspherical or irregular shaped particles which are typically produced by a bulk polymerization process. It is believed the reason that macrostructures made exclusively from spherical shaped particles of hydrogel-forming absorbent polymer are prone to gel block is due to the formation of a close, compacted structure that would have poorer fluid permeability. It has been found that the inclusion of nonspherical (irregular) shaped particles seems to perturb the self-assembling nature of the spherical shaped particles during the making of the macrostructures, especially macrostructures in sheet form. As a result, the macrostructure is no longer prone to blocking fluid.

Generally, these mixtures according to variant (2) comprise from about 5 to about 50% of the spherical particles and from about 50 to about 95% the nonspherical particles. Preferably, these mixtures comprise from about 10 to about 50% of the spherical particles and from about 50 to about 90% the nonspherical particles, more preferably from about 20 to about 40% of the spherical particles and from about 60 to about 80% of the nonspherical particles.

Spherical shaped particles and spherical shaped agglomerates can be obtained by multi-phase polymerization processing techniques such as inverse emulsion polymerization or inverse suspension polymerization procedures. In the inverse emulsion polymerization or inverse suspension polymerization procedures, the aqueous reaction mixture is suspended in the form of tiny droplets in a matrix of a water-immiscible, inert organic solvent such as cyclohexane. The resultant precursor particles are generally spherical in shape. Inverse suspension polymerization procedures are disclosed in U.S. Pat. No. 4,093,776 (Aoki et al), issued Jun. 6, 1978, U.S. Pat. No. 4,340,706 (Obaysashi et al), issued Jul. 20, 1982, U.S. Pat. No. 4,446,261 (Yamasaki et al), issued, U.S. Pat. No. 4,506,052 (Flesher et al), issued Mar. 19, 1985, U.S. Pat. No. 4,541,871 (Obayashi et al), issued Sep. 17, 1985, U.S. Pat. No. 4,698,414 (Cramm et al), issued Oct. 6, 1987, U.S. Pat. No. 4,735,987 (Morita et al), issued Apr. 5, 1988, U.S. Pat. No. 4,833,179 (Young et al), issued May 23, 1989, and European Patent Application 522,570, published Jan. 13, 1993. Suitable spherical shaped particles of hydrogel-forming absorbent polymer include F201 made by Nippon Gohsei and Base 60 made by Mitsubishi Chemical.

Nonspherical or irregular shaped particles can be obtained by bulk polymerization procedures including aqueous solution or other solution polymerization methods. As described in the above-referenced U.S. Reissue Pat. No. 32,649, aqueous solution polymerization involves the use is of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles. Suitable nonspherical shaped particles of hydrogel-forming absorbent polymer include L76If made by Nippon Shokubai, SXP or SXM made by Chemische Fabrik Stockhausen, and 1180 or XP 30 made by Nalco Chemical.

D. Crosslinking Agents

In preparing macrostructures according to the present invention, a crosslinking agent is used to provide crosslinking at the surface of the mixture of absorbent precursor particles. This typically occurs as a result of reacting the crosslinking agent with the polymer material in these particles. Typically, the polymer material of the absorbent precursor particles has anionic, and preferably carboxy, functional groups that form a covalent, ester-type bond with the crosslinking agent. These portions of the absorbent particle that have been effectively crosslinked will swell less in the presence of aqueous (body) fluids relative to the other uncrosslinked portions of the particle.

Suitable crosslinking agents for this purpose can be nonionic and possess at least two functional groups per molecule capable of reacting with the carboxy group. See, for example, U.S. Pat. No. 5,102,597 (Roe et al), issued Apr. 7, 1992, which discloses a variety of nonionic crosslinking agents that include polyhydric alcohols such as ethylene glycol, diethylene glycol, triethylene glycol, tetraethylene glycol, polyethylene glycol, glycerol (1, 2, 3-propanetriol), polyglycerol, propylene glycol, 1, 2-propanediol, 1, 3-propanediol, trimethylol propane, diethanolamine, triethanolamine, polyoxypropylene oxyethylene-oxypropylene block copolymer, sorbitan fatty acid esters, polyoxyethylene sorbitan fatty acid esters, pentaerythritol, and sorbitol; polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and propylene glycol diglycidyl ether; polyaziridine compounds such as 2, 2-bishydroxymethyl butanol-tris [3-(i-aziridine) propionate], 1, 6-hexamethyl toluene diethylene urea, and diphenyl methane-bis-4, 4'-N,N'-diethylene urea; haloepoxy compounds such as epichlorohydrin and a-methylfluorohydrin; polyaldehyde compounds such as glutaraldehyde and glyoxazole; polyamine compounds such as ethylene diamine, diethylene triamine, triethylene tetramine, tetraethylene pentamine, pentaethylene hexamine, and polyethylene imine; and polyisocyanate compounds such as 2, 4-toluene diisocyanate and hexamethylene diisocyanate. The particularly preferred nonionic crosslinking agent is glycerol A preferred crosslinking agent for use in the present invention is an adduct of epichlorohydrin with certain types of monomeric or polymeric amines. See U.S. Pat. No. 5,324,561 (Rezai et al), issued Jun. 23, 1994, which discloses suitable cationic amino-epichlorohydrin adduct crosslinking agents. These amino-epichlorohydrin adducts, and especially the polymeric resin versions of these adducts, are preferred crosslinking agents because they react only with the polymer material at the surface precursor particles. In addition, the cationic functional groups (e.g., azetedinium groups) of these adducts, particularly polymeric resin versions, are believed to react very rapidly with the anionic, typically carboxy, functional groups of the polymer material of the absorbent particles, even at room temperature (e.g., at from about 18° to about 25° C.). As a result, fairly modest levels (e.g., as low as about 1% by weight of the particles) of these amino-epichlorohydrin adducts are required to provide effective surface crosslinking of the polymer material present in the absorbent precursor particles.

Suitable cationic amino-epichlorohydrin adducts useful as crosslinking agents include those where epichlorohydrin are reacted with monomeric di-, tr- and higher amines having primary or secondary amino groups in their structure such as bis-2-aminoethyl ether, N,N-dimethylethylenediamine, piperazinei ethylenediamine; N-aminoethyl piperazine, and dialkylene triamines such as diethylenetriamine, and dipropylenetriamine; polymeric amines such as polyethyleneimines, and certain polyamide-polyamines derived from polyalkylene polyamines and saturated $C_3$–$C_{10}$ dibasic carboxylic acids. These epichlorohydrin/polyamide-polyamine adducts are well known in the art as wet strength resins for paper products. More preferred epichlorohydrin/polyamide-polyamine adducts are those derived from the polyethylene polyamines containing from two to four ethylene groups, two primary amine groups, and from one to three secondary amine groups, and saturated aliphatic $C_3$–$C_{10}$ dicarboxylic acids, more preferably those containing from 3 to 8 carbon atoms, such as malonic, succinic, glutaric, adipic, together with diglycolic acid. Cationic polyamide-polyamine-epichlorohydrin resins particularly preferred for use herein as crosslinking agents are commercially marketed by Hercules Inc. under the trade name KYMENE. Especially useful are KYMENE 557H, KYMENE 557LX and KYMENE 557 PLUS, which are the epichlorohydrin adducts of polyamide-polyamines which are the reaction products of diethylenetriamine and adipic acid. They are typically marketed in the form of aqueous solutions of the cationic resin material containing from about 10% to about 33% by weight of the resin active.

E. Preparation of Interparticle Bonded Aggregates and Macrostructures

In preparing the interparticle bonded aggregates that comprise the porous, absorbent macrostructures, the mixture of absorbent precursor particles are treated with a sufficient amount of the crosslinking agent to react with the polymer material at the surface of the particles so as to cause effective crosslinking, i.e., the crosslinked surface of the particle swells less in the presence of aqueous body fluids relative to the uncrosslinked portions. What constitutes "a sufficient amount" of the crosslinking depends upon a number of factors, including the particular absorbent precursor particles treated, the crosslinking agent used, the particular effects desired in forming the interparticle bonded aggregate, and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents).

Besides the absorbent precursor particles and the crosslinking agent, other components or agents can be used as aids in preparing the interparticle bonded aggregates. For example, water is typically used with the crosslinking agent to form an aqueous treatment solution thereof. Water promotes the uniform dispersion of the crosslinking agent on the surface of the precursor particles and causes permeation of the crosslinking agent into the surface regions of these particles. Water also promotes a stronger physical association between the treated precursor particles, providing greater integrity of the resultant interparticle bonded crosslinked aggregates. The actual amount of water used can vary depending upon the type of crosslinking agent used, the type of polymer material used in forming the precursor particles, the particle size of these precursor particles, the inclusion of other optional components (e.g., glycerol) and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents).

Although not absolutely necessary, organic solvents can be used, usually to promote uniform dispersion of the crosslinking agent onto the surface of the precursor particles. These organic solvents are typically hydrophilic, and can include lower alcohols such as methanol and ethanol; amides such as N,N-dimethylformamide and N,N-diethylformamide; and sulfoxides such as dimethylsulfoxide. The actual amount of hydrophilic solvent used can vary depending upon the adduct used, the polymer material used forming the precursor particles, the particle size of these precursor particles and like factors. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents).

Other optional components can also be used with the crosslinking agent, and especially aqueous treatment solutions thereof. It is particularly preferred that the treatment solution include a plasticizer, especially when cationic amino-epichlorohydrin adducts are used as the crosslinking agent. See U.S. Pat. No. 5,324,561 (Rezai et al), issued Jun. 23, 1994. Suitable plasticizers include water, alone or in combination with other components such as glycerol, propylene glycol (i.e. 1,2-propanediol), 1,3propanediol, ethylene glycol, sorbitol, sucrose, polymeric solutions such as those involving polyvinyl alcohol, ester precursors of polyvinyl alcohol, or polyethylene glycol, or mixtures thereof. These other components in the plasticizer, such as glycerol, are believed to act as humectants, coplasticizers or both, with water being the primary plasticizer. The preferred plasticizer for use in the present invention is a mixture of glycerol and water, particularly when included as part of an aqueous treatment solution of the cationic amino-epichlorohydrin adduct, in a weight ratio of glycerol to water of from about 0.5:1 to about 2:1, preferably from about 0.8:1 to about 1.7:1.

The actual amount of plasticizer used can vary depending upon the particular plasticizer used, the type of polymer material used in forming the precursor particles, and the particular flexibility effects desired from the plasticizer. Typically, the plasticizer is used in an amount of from about 5 to about 100 parts by weight, preferably from about 5 to about 60 parts by weight, more preferably from about 10 to about 30 parts by weight, more preferably from about 15 to about 20 parts by weight, per 100 parts by weight of the precursor particles. See U.S. Pat. No. 5,324,561 (Rezai et al), issued Jun. 23, 1994.

In the method of the present invention, the absorbent precursor particles can be treated with the cationic amino-epichlorohydrin adduct, typically an aqueous solution thereof, by any of a variety of techniques. These include any method for applying solutions to materials, including coating, dumping, pouring, dropping, spraying, atomizing, condensing, or immersing the absorbent precursor particles with the cationic amino-epichlorohydrin adduct, or solution thereof. "Applied" means that at least a portion of the surface area of at least some of the precursor particles to be bonded together has an effective amount of the adduct on it to cause surface crosslinking. In other words, the cationic adduct can be applied onto some of the precursor particles, all of the precursor particles, a portion of the surface of some or all of the precursor particles, or the entire surface of some or all of the precursor particles. Preferably, the adduct is coated onto the entire surface of most, preferably all, of the absorbent precursor particles so as to enhance the efficiency, strength, and density of the interparticle bonds between the precursor particles, as well as the desired surface crosslinking of the polymer material in the surface of these precursor particles.

After the treatment solution has been applied onto the precursor particles, the treated precursor particles can be mixed or layered together by any of a number of mixing or layering techniques to insure that the precursor particles are thoroughly coated with the treatment solution. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents). Before, during, or after applying the treatment solution, the precursor particles are physically associated together to form an aggregate macrostructure. The precursor particles are preferably physically associated together by applying an associating agent onto the precursor particles and physically contacting the precursor particles at least to the portion of the surface of the precursor particles having the associating agent applied thereto. Associating agents useful in the present invention include hydrophilic organic solvents, typically low molecular weight alcohols such as methanol or ethanol; water; a mixture of hydrophilic organic solvents and water; the crosslinking agents, or mixtures thereof. Preferred associating agents are water, methanol, ethanol, cationic polymeric amino-epichlorohydrin resins such as KYMENE 557H, or 557LX or PLUS, or mixtures thereof. Typically the associating agent comprises a mixture including the crosslinking agent such that the step of applying the crosslinking is carried out simultaneously with the step of applying the associating agent.

The associating agents can be applied to the precursor particles by any of various techniques and apparatus used for applying solutions to materials including coating, dumping, pouring, spraying, atomizing, condensing, or immersing the associating agent on the precursor particles. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents). When an associating agent has been applied to the precursor particles, the precursor particles can be physically contacted together in a number of different ways. For example, the associating agent alone can hold the particles together in contact. Alternatively, gravitational forces can be used to insure contact between the precursor particles, e.g., by layering precursor particles. Further, the particles can be placed in a container having a fixed volume so as to insure contact between the precursor particles.

The precursor particles can alternatively be physically associated together by physically constraining the precursor particles such that they are in contact with each other. For example, the precursor particles can be packed tightly into a container having a fixed volume such that the precursor particles physically contact each other. Alternatively or in combination with the above procedure, gravitational forces (e.g., layering) can be used to physically associate the precursor particles. The precursor particles can also be physically associated together by electrostatic attraction or by the introduction of an adhering agent (e.g., an adhesive material such as a water-soluble adhesive) to adhere them together. The precursor particles can also be attached to a third member (a substrate) such that the precursor particles are brought into contact with each other by the substrate.

In an alternative method of forming the macrostructures of the present invention, the aggregate of the precursor particles is shaped into various geometries, spatial relationships, and densities to form an aggregate having a defined shape, size, and/or density. The aggregate can be shaped by any conventional shaping techniques as are known in the art. Preferred methods for shaping the aggregate include casting, molding, or forming operations. Casting and molding techniques generally involve introducing the precursor particles into a prepared mold cavity and applying pressure to (compressing) the aggregate to cause the aggregate to conform to the shape of the mold cavity. Examples of specific molding techniques for use herein include compression molding, injection molding, extrusion or laminating. For example, a multiplicity of precursor particles can be added to a container having a fixed volume mold cavity and the aggregate compressed to conform to the shape of the mold cavity so that the resultant macrostructure has the same shape. Forming techniques involve performing various operations on the aggregate to modify its shape, and/or size, and/or density. Examples of specific forming techniques for use herein include rolling, forging, extruding, spinning, coating or drawing operations. For example, an aggregate mixture of the precursor particles and at least the cationic amino-epichlorohydrin adduct can be passed between a pair of compaction rolls to form an aggregate sheet. Alternatively, the aggregate mixture can be extruded through an orifice to form an aggregate having a shape corresponding to that of the orifice. Further, the aggregate mixture can be cast on a surface to form an aggregate having a desired shape or surface morphology. Any or all of these techniques can also be used in combination to form the shaped aggregate. Any suitable apparatus as are known in the art can be used to carry out such operations, which can be performed with the material or portions of the apparatus either hot and/or cold. A preferred method and apparatus for continuously forming the aggregate macrostructures of the present invention into sheets is described in U.S. Pat. No. 5,324,561 (Rezai et al), issued Jun. 23, 1994 (cationic amino-epichlorohydrin adduct crosslinking agents). See especially FIG. 9 from U.S. Pat. No. 5,324,561 and its associated description.

Simultaneously or after the treatment solution has been applied, the precursor particles have been physically associated together to form an aggregate, and the aggregate has been shaped, the crosslinking agent is reacted with the polymer material of the precursor particles, while maintaining the physical association of the precursor particles, to provide effective surface crosslinking in the precursor particles in the aggregate macrostructure. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents). Because of the relatively reactive cationic functional groups of the amino-epichlorohydrin adducts that can be used as crosslinking agents in the present invention, this crosslinking reaction can occur at relatively low temperatures, including ambient room temperatures. Such ambient temperature curing is particularly desirable when the treatment solution additionally contains a plasticizer, such as a mixture of water and glycerol. Curing at significantly above ambient temperatures can cause the plasticizer to be driven off due to its volatility, thus necessitating an additional step to plasticize the resulting interparticle bonded aggregate. Such ambient curing is typically carried out at a temperature of from about 18° to about 35° C. for from about 12 to about 48 hours. Preferably, such ambient curing is carried out at a temperature of from about 18° to about 25° C. for from about 24 to about 48 hours.

Although the crosslinking reaction can occur at ambient temperatures, such curing can also be carried out at higher temperatures to speed up the reaction. Higher temperature curing typically involves heating the treated and associated precursor particles to cause the crosslinking reaction to occur in a shorter period of time, typically minutes. This heating step can be carried out using a number of conventional heating devices, including various ovens or dryers well known in the art.

Generally, heat curing can be carried out at a temperature above about 50° C. for a period of time sufficient to complete the crosslinking reaction. The particular temperatures and times used in heat curing will depend upon the particular crosslinking agents used and the polymer material present in the precursor particles. See U.S. Pat. No. 5,102,597 (Roe et al), issued Apr. 7, 1992 (nonionic crosslinking agents such as glycerol), and U.S. Pat. No. 5,324,561 (Rezai et al), issued Jun. 23, 1994 (cationic amino-epichlorohydrin adduct crosslinking agents). In the case of the preferred cationic amino-epichlorohydrin adducts, heat curing is generally carried out at a temperature in the range of from about 50° to about 205° C. for from about 1 to about 20 minutes. Preferably, heat curing is carried out at a temperature of from about 180° to about 200° C. for from about 5 to about 15 minutes.

The physical association of the treated precursor particles needs to be maintained during the curing step so that, as crosslinking occurs, adjacent precursor particles become cohesively bonded together. If forces or stresses are sufficient to disassociate the precursor particles that are present during the crosslinking reaction, insufficient bonding of the precursor particles can occur. This can result in aggregates having poor structural integrity. The physical association of the precursor particles is typically maintained by insuring minimal dissociation forces or stresses are introduced during the curing step.

The steps for producing the macrostructures need not be carried out in any specific order, and can be carried out simultaneously. For example, the treatment solution can be applied simultaneously with the physical association of the precursor particles, shaped into a preferred shape and typically a desired density, and then the crosslinking agent reacted with the polymer material of the precursor particles, either immediately after the above steps are completed or after the aggregate has been left standing for a period of time, to simultaneously surface crosslink the precursor particles and form the aggregate macrostructure. Typically, the precursor particles are mixed or sprayed with a solution of the crosslinking agent, water, a humectant and/or coplasticizer (e.g., glycerol), and a hydrophilic organic solvent (e.g., methanol) to form an adhered together aggregate. The adhered aggregate (i.e. the associated precursor particles and the aqueous mixture) is subsequently shaped into a densified sheet by a combination of extruding and rolling techniques as described above. The crosslinking agent is subsequently reacted with the polymer material by ambient or heat curing to simultaneously cause crosslinking at the surface of the precursor particles and to form a cohesive interparticle bonded aggregate macrostructure.

The macrostructures can also be treated with a plasticizer after curing to effect surface crosslinking. Suitable plasticizers include water, alone or in combination with the humectants/coplasticizers previously described, preferably glycerol. The plasticizer can be applied to the macrostructures in a number of different ways, including spraying, coating, atomizing, immersing, or dumping the plasticizer onto the macrostructure. Alternatively, in the case of water alone, the macrostructure can be placed in a high humidity environment (e.g., greater than 70% relative humidity). The amount of plasticizer applied to the macrostructure can be selected depending upon the specific plasticizer used, and the effects desired. Typically, the amount of plasticizer applied is from about 5 to about 100 parts by weight, preferably from about 5 to about 60 parts by weight, per 100 parts by weight of the macrostructure. A particularly preferred plasticizer comprises a mixture of glycerol and water in a weight ratio of from about 0.5:1 to about 2:1, preferably from about 0.8:1 to about 1.7:1.

Various types of fiber material can be used as the reinforcing members in the macrostructures of the present invention. Any type of fiber material which is suitable for use in conventional absorbent products is also suitable for use in the macrostructures herein. Specific examples of such fiber material include cellulose fibers, modified cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the macrostructures of the present invention by virtue of their good wicking properties. This is because, in the macrostructures herein, the wicking propensity of the fibers is as important, if not more important, than the absorbent capacity of the fiber material itself due to the high rate of fluid uptake and lack of gel blocking properties of the macrostructures of the present invention. Synthetic fibers are generally preferred for use herein as the fiber component of the macrostructure. More preferred are polyolefin fibers, preferably polyethylene fibers.

Other cellulosic fiber materials which can be useful in certain macrostructures herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889,596 (Schoggen. et al), issued Dec. 26, 1989; U.S. Pat. No. 4,889,597 (Bourbon et al), issued Dec. 26, 1989; and U.S. Pat. No. 4,898,647 (Moore et al), issued Feb. 6, 1990.

"Hydrophilic" describes fibers or the surfaces of fibers which are wetted by the liquids deposited onto the fibers (i.e., if water or aqueous body fluid readily spreads on or over the surface of the fiber without regard to whether or not the fiber actually imbibes fluid or forms a gel). The state of the art respecting wetting of materials allows definition of hydrophobicity (and wetting) in terms of contact angles and the surface tension of the liquids and solids involved. This is discussed in detail in the American Chemical Society Publication entitled "CONTACT ANGLE, WETTABILITY, AND ADHESION", edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

The fiber material can be added to the macrostructures by introducing the fibers into the treatment solution with the crosslinking, by mixing with the precursor particles prior to applying the treatment solution, or by adding the fiber material to the treatment solution/precursor particle mixture. For example, the fiber material can be kneaded into the treatment solution/precursor particle mixture. The fiber material is preferably thoroughly mixed with the solution so that the fiber material is uniformly dispersed throughout the macrostructure. The fibers are also preferably added before reacting the adduct with the polymer material of the precursor particles.

F. Optional Substrate Layer

If desired, the porous absorbent macrostructure can be attached to an optional substrate. See copending U.S. application Ser. No. 142,253 (Hsueh et al), filed Oct. 22, 1993. The substrate can provide a variety of functions, including: (1) improving the distribution of fluids to be absorbed by the macrostructure; and (2) supporting the macrostructure by providing additional integrity, especially in the situation where the absorbent particles begin to swell after absorbing fluid. The substrate can be made from various materials known in the art such as cellulose fibers, nonwoven webs, tissue webs, foams, polyacrylate fibers, apertured polymeric webs, synthetic fibers, metallic foils, elastomers, and the like. Most such substrate materials can distribute fluids to, as well as support the macrostructure. Preferably, the substrate is comprised of cellulosic material or a material having cellulosic functionality. Preferred substrates for distributing fluids are cellulosic materials, fibrous webs, cellulosic fibrous webs, solid foams, cellulosic foams, and polyvinyl alcohol foams. Preferred substrates for supporting the macrostructure are cellulosic materials, fibrous webs, nonwoven webs, fabrics, cellulosic fibrous webs, solid foams, cellulosic foams, and polyvinyl alcohol foams.

The substrate is preferably flexible and pliable to encourage such properties in the resulting absorbent composite with the macrostructure. The substrate can be substantially resilient and non-stretchable, or it can be stretchable or deformable to a varying extent in response to forces exerted normal to and in the plane of the surface of the substrate. The thickness and basis weight (weight per unit area of substrate) of the substrate material can vary depending on the type of substrate and properties desired. The substrate can comprise a plurality of individual sheets, or plies, of a particular substrate material, or a combination of one or more substrate layers in a laminate. One such suitable substrate is a BOUNTY® sheet having a thickness of from about 0.02 mm to about 1.2 mm, more preferably from about 0.3 mm to about 0.8 mm, and a basis weight of from about 5 gm/m$^2$ to about 100 gm/m$^2$, more preferably from about 10 gm/m$^2$ to about 60 gm/m$^2$, and more preferably from about 15 gm/m$^2$ to about 40 gm/m$^2$. Another suitable substrate is a cellulose foam having a dry compressed thickness of from about 0.5 mm to about 3.0 mm, more preferably from about 0.8 mm to about 2.0 mm, a wet expanded thickness of from about 0.8 mm to about 6.0 mm, more preferably from about 1.0 mm to about 5.0 mm, and a basis weight of from about 50 gm/m$^2$ to about 2,000 gm/m$^2$, more preferably from about 100 gm/m$^2$ to about 1,000 gm/m$^2$.

Substrates suitable for supporting the macrostructure typically have a dry tensile strength of from about 500 gm/in to about 8,000 gm/in, more preferably from about 1,000 gm/in to about 3,000 gm/in, a wet tensile strength of from about 200 gm/in to about 5,000 gm/in, though more preferably from about 400 gm/in to about 1,000 gm/in, and a wet burst strength of from about 100 gm to about 2,000 gm, though more preferably from about 200 gm to about 1,000 gm. Preferred substrates of this type include cellulosic fibrous webs such as paper towels and tissues such those disclosed in U.S. Pat. No. 3,953,638, issued Apr. 27, 1976, U.S. Pat. No. 4,469,735, issued Sep. 4, 1984, U.S. Pat. No. 4,468,428, issued Aug. 28, 1984, and U.S. Pat. No. 4,986,882, issued Jan. 22, 1991. Another preferred substrate layer of this type is a cellulosic foam since it provides a higher fluid wicking rate over a longer wicking distance than a cellulosic fibrous web. Preferably, the cellulosic foam is in a compressed state so as to further improve its fluid wicking and distribution properties. Suitable cellulose foams can be made of regenerated rayon fibers by well-known methods, such as those disclosed in European patent application 293,208 (Uchida et al), published Nov. 30, 1988.

The porous absorbent macrostructure can be attached to the substrate by a variety of chemical, physical, and adhesive agents. Adhesive agents for attaching the substrate to the macrostructure include glues and hot melt adhesives. Preferably, the bonding between the substrate and macrostructure is achieved by depositing the precursor absorbent particles on the substrate, treating the deposited particles with the solution comprising a crosslinking agent and then curing the treated particles/substrate as previously discussed. In a preferred embodiment of this method, a cellulosic substrate (e.g., paper towel) is used. The precursor absorbent particles are then deposited on this cellulosic substrate. A treatment solution comprising an aminoepichlorohydrin adduct, preferably polymeric epichlorohydrin-polyamide/polyamine wet strength resin such KYMENE, is then applied (e.g., sprayed) on the cellulosic substrate and the absorbent. The treated substrate/particles are then cured at ambient temperatures such that a porous macrostructure is formed that is bonded to the cellulosic substrate.

G. Treating Macrostructure With Latex to Improve Flexibility

Optionally, the above absorbent macrostructures (with or without the optional substrate) can be treated with certain latexes. "Latex" refers to an aqueous dispersion or emulsion of polymer particles in an aqueous phase, and can also be referred to as an emulsion polymer. "Sinter" refers to the fusion mechanism which occurs upon the drying of a suspended liquid emulsion or dispersion such as a latex; the use of "sinter" is synonymous with the phrase "film forming." Treatment of these macrostructures with these latexes has been found to dramatically increase the flexibility of the macrostructure, especially when in the form of a sheet and even when attached to a substrate such as a paper towel. In addition to improved flexibility, latex treatment according to the present invention improves the bonding between particles of the aggregates that comprise these macrostructures. This leads to improvements in the dry and wet integrity of the macrostructure. The presence of the latex also allows these macrostructures to be thermally bonded to nonwovens, such as the backsheet of an absorbent article (e.g., a diaper).

It has been found that latexes suitable for use in the present invention need to have certain properties. One key property of these latexes is that they be "rubbery" at ambient temperatures or below after they have been sintered. In other words, latexes useful in the present invention have a glass transition temperature (Tg) of about 25° or less. Preferably, these latexes have a Tg of about 10° C. or lower and, more preferably of about −10° C. or lower. Another important property of these latexes is the temperature at which they are capable of being sintered. Latexes useful in the present invention need to be sinterable at ambient temperatures or below. In other words, it is preferable for these latexes to be sinterable at a temperature of about 25° C. or lower. The ability of the latex to be sinterable at ambient temperatures is important in avoiding drying out the macrostructure. Another important property of these latexes is their hydrophilicity. To be useful in the present invention, the latex, when sintered needs to be at least somewhat hydrophilic. "Hydrophilic" describes a material, or surface of a material, that is wettable by aqueous fluids (e.g., aqueous body fluids) deposited on these materials. Hydrophilicity and wettability are typically defined in terms of contact angle and the surface tension of the fluids and solids involved. This is discussed in detail in the American Chemical Society publication entitled CONTACT ANGLE, WETTABILITY AND ADHESION, edited by Robert F. Gould (Copyright 1964).

Latexes useful in the present invention are typically prepared by emulsion polymerization of certain olefinic (ethylenically unsaturated) monomers. This emulsion polymerization can be carried out by customary methods using any of a variety anionic, nonionic, cationic, zwitterionic and/or amphoteric emulsifiers to stabilize the resultant latex, including alkyl sulfates, alkylarylalkoxy sulfates, alkylarylsulfonates and alkali metal and/or ammonium salts of alkyl- and alkylaryl-polyglycol ether-sulfates; oxyethylated fatty alcohols or oxyethylated alkylphenols, as well as block copolymers of ethylene oxide and propylene oxide; cationic adducts of primary, secondary or tertiary fatty amines or fatty amine oxyethylates with organic or inorganic acids, and quaternary alkylammonium surfactants; and alkylamidopropylbetaines. The olefinic monomer can be a single type of monomer or can be mixture of different olefinic monomers, i.e. to form copolymer particles dispersed or emulsified in the aqueous phase. The latex suitable for use herein is preferably neutral or has no ionic charge, vis-a-vis, the latex is not cationic or anionic in nature.

Suitable latexes can be prepared via emulsion polymerization from olefinic monomers that include the $C_2$ to $C_4$ alkyl and hydroxy alkyl acrylates, such as those selected from the group of propyl acrylate, n-butyl acrylate, isobutyl acrylate, 2-hydroxyethyl acrylate, 2-hydroxypropyl acrylate, ethyl acrylate and mixtures thereof. Also suitable are $C_1$ to $C_4$ alkyl or hydroxy alkyl methacrylates selected from the group of propyl methacrylate, n-butyl methacrylate, isobutyl methacrylate, 2-hydroxyethyl methacrylate, 2-hydroxypropyl methacrylate, ethyl methacrylate, methyl methacrylate, vinyl acetate and mixtures thereof. Also suitable are mixtures of the aforementioned $C_2$ to $C_4$ alkyl and hydroxy alkyl acrylates and $C_1$ to $C_4$ alkyl or hydroxy alkyl methacrylates. Especially suitable for use in the invention is an emulsion of polymethyl methacrylate. Particularly preferred latexes include those sold under the tradename MONWINYL 963 by Hoechst Celanese and RHOPLEX E1845 by Rohm & Haas.

In preparing the porous absorbent macrostructures of the present invention having improved flexibility, the macrostructure is treated with an effective amount of these latexes to coat at least some of the absorbent particles. What constitutes a "effective amount" will depend on a variety of factors, including the particular porous absorbent macrostructure involved, the particular latex used, the flexibility benefits desired, and like factors. More preferably, treating the macrostructure with about 2% by weight latex will be sufficient to impart noticeable improvements in the flexibility of the macrostructure. However, the macrostructure can be effectively treated with from about 1% to about 10% by weight, and more preferably from about 2% to about 5% by weight of latex.

The porous absorbent macrostructure can be treated with the latex by any of the variety of methods suitable for applying additives to conventional substrates. Suitable methods includes spraying, printing (e.g., flexographic printing), coating, e.g., gravure coating, dipping, brushing, foaming or combinations of such application techniques. Typically, the latex is sprayed onto the already formed porous absorbent macrostructure and then sintered at ambient temperature, e.g., at about 25° C. or lower. Additionally, latex treatment can assist in the forming of a more stable macrostructure by providing improved particle immobilization.

Besides spraying on the latex on the already formed, macrostructure, other methods can also be used to treat the porous absorbent macrostructure with the latex. One such method involves blending the latex with the untreated precursor absorbent particles and then treating this latex/particle blend with the solution containing the crosslinking agent plus any other optional components such as glycerol. This treated latex/particle blend can then be cured at ambient temperature, e.g., at about 25° C. or lower, to provide porous absorbent macrostructure having improved flexibility.

Another method involves casting the latex as a thin film. The precursor absorbent particle can then be deposited onto this cast film. The cast film with the deposited particles is then treated (such as by spraying) with a solution containing crosslinking agent and any other optional components. This treated particle/latex film can then be cured at ambient temperature, e.g., at about 25° C. or lower, to provide porous absorbent macrostructure having improved flexibility. In addition, the sintered latex film can function as a supporting substrate for the macrostructure to provide dry and especially wet integrity.

Yet another method involves pressurizing latex in a container such that it can be blown or sprayed onto the precursor particles in the form of a foam, after which a compression roll or the like is used to spread the latex evenly. The blown or sprayed foam latex is, to some extent, in the form of porous fibers which are extremely porous and further enhance the absorbency of the macrostructure. A latex treated macrostructure of this type, in which the precursor particles swell into the porous latex fibers, has improved structural integrity.

III. Uses of Macrostructures

The porous, absorbent macrostructures of the present invention can be used for many purposes in many fields of use. For example, the macrostructures can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Figure 3:
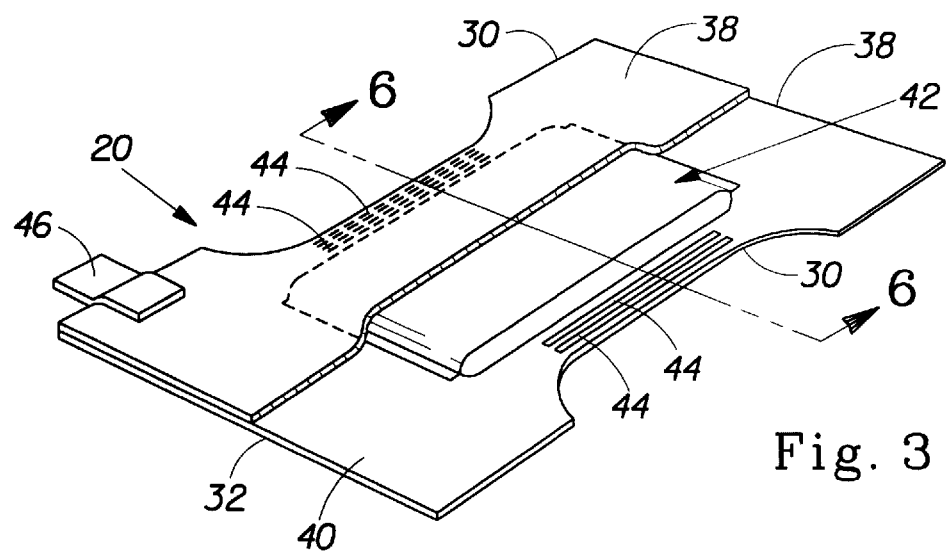
FIG. 3 is a perspective view of a disposable diaper embodiment according to the present invention wherein portions of the topsheet have been cut-away to more clearly show the underlying absorbent core (an embodiment of an absorbent member according to the present invention) of the diaper wherein the absorbent member comprises a porous, absorbent macrostructure according to the present invention.

Because of the unique absorbent properties of the porous, absorbent macrostructures of the present invention, they are especially suitable for use as absorbent cores in absorbent articles, especially disposable absorbent articles. "Absorbent article" refers to articles which absorb and contain body exudates and more specifically refers to articles which are placed against or in proximity to the body of the wearer to absorb and contain the various exudates discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article, diaper 20, is shown in FIG. 3. "Diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 3 is a perspective view of the diaper 20 of the present invention in its uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 3 to preferably comprise a liquid pervious topsheet 38; a liquid impervious backsheet 40 joined with the topsheet 38; an absorbent core 42 positioned between the topsheet 38 and the backsheet 40; elastic members 44; and tape tab fasteners 46. While the topsheet 38, the backsheet 40, the absorbent core 42, and the elastic members 44 can be assembled in a variety of well known configurations, a preferred diaper configuration is described generally in U.S. Pat. No. 3,860,003 (Buell), issued Jan. 14, 1975. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989.

FIG. 3 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby forming the periphery of the diaper 20. The periphery defines the outer perimeter or the edges of the diaper 20. The periphery comprises the end edges 32 and the longitudinal edges 30.

The topsheet 38 is compliant, soft feeling, and non-irritating to the wearer's skin. Further, the topsheet 38 is liquid pervious permitting liquids to readily penetrate through its thickness. A suitable topsheet 38 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. "Staple length fibers" refers to those fibers having a length of at least about 15.9 mm (0.62 inches).

There are a number of manufacturing techniques which can be used to manufacture the topsheet 38. For example, the topsheet 38 can be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent core 42 from wetting articles which contact the diaper 20 such as bedsheets and undergarments. Preferably, the backsheet 40 is polyethylene film having a thickness from about 0.012 mm (0.5 mil) to about 0.051 centimeters (2.0 mils), although other flexible, liquid impervious materials can be used. "Flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery.

The topsheet 38 and the backsheet 40 are joined together in any suitable manner. "Joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 38 to the backsheet 40.

Tape tab fasteners 46 are typically applied to the back waistband region of the diaper 20 to provide a fastening means for holding the diaper on the wearer. The tape tab fasteners 46 can be any of those well known in the art, such as the fastening tape disclosed in U.S. Pat. No. 3,848,594 (Buell), issued Nov. 19, 1974. These tape tab fasteners 46 or other diaper fastening means are typically applied near the corners of the diaper 20.

The elastic members 44 are disposed adjacent the periphery of the diaper 20, preferably along each longitudinal edge 30, so that the elastic members 44 tend to draw and hold the diaper 20 against the legs of the wearer. Alternatively, the elastic members 44 can be disposed adjacent either or both of the end edges 32 of the diaper 20 to provide a waistband as well as or rather than leg cuffs. For example, a suitable waistband is disclosed in U.S. Pat. No. 4,515,595 (Kievit et al), issued May 7, 1985. In addition, a method and apparatus suitable for manufacturing a disposable diaper having elastically contractible elastic members is described in U.S. Pat. No. 4,081,301 (Buell), issued Mar. 28, 1978.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 can be stretched and secured while the diaper 20 is in an uncontracted condition. Alternatively, the diaper 20 can be contracted, for example, by pleating, and the elastic members 44 secured and connected to the diaper 20 while the elastic members 44 are in their unrelaxed or unstretched condition.

In the embodiment illustrated in FIG. 3, the elastic members 44 extend along a portion of the length of the diaper 20. Alternatively, the elastic members 44 can extend the entire length of the diaper 20, or any other length suitable to provide an elastically contractible line. The length of the elastic members 44 is dictated by the diaper design.

The elastic members 44 can be in a multitude of configurations. For example, the width of the elastic members 44 can be varied from about 0.25 millimeters (0.01 inches) to about 25 millimeters (1.0 inch) or more; the elastic members 44 can comprise a single strand of elastic material or can comprise several parallel or non-parallel strands of elastic material; or the elastic members 44 can be rectangular or curvilinear. Still further, the elastic members 44 can be affixed to the diaper in any of several ways which are known in the art. For example, the elastic members 44 can be ultrasonically bonded, heat and pressure sealed into the diaper 20 using a variety of bonding patterns or the elastic members 44 can simply be glued to the diaper 20.

The absorbent core 42 of the diaper 20 is positioned between the topsheet 38 and the backsheet 40. The absorbent core 42 can be manufactured in a wide variety of sizes and shapes (e.g., rectangular, hourglass, asymmetrical, etc.) and from a wide variety of materials. The total absorbent capacity of the absorbent core 42 should, however, be compatible with the design liquid loading for the intended use of the absorbent article or diaper. Further, the size and absorbent capacity of the absorbent core 42 can vary to accommodate wearers ranging from infants through adults. The absorbent core 42 comprises the porous, absorbent macrostructures of the present invention.

Figure 4:
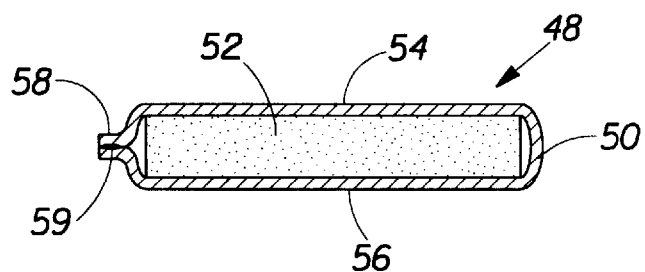
FIG. 4 is a cross-sectional view of the absorbent core of the diaper shown in FIG. 3 taken along sectional line 6—6 of FIG. 3.

A preferred embodiment of the diaper 20 has a rectangular-shaped absorbent core 42. As shown in FIG. 4, the absorbent core 42 preferably comprises an absorbent member 48 comprising an envelope web 50 and a porous, absorbent macrostructure 52 disposed in the envelope web 50. The macrostructure 52 is encased in the envelope web 50 to minimize the potential for the precursor particles to migrate through the topsheet and to provide an additional liquid transport layer between the topsheet 38 and the macrostructure 52 to enhance liquid acquisition and minimize rewet. As shown in FIG. 4, a single envelope web 50 is wrapped about the macrostructure 52 by folding to form a first layer 54 and a second layer 56. The edges 58 of the envelope web 50 are sealed about its periphery by any conventional means such as an adhesive 59 (as shown), ultrasonic bonds, or heat/pressure bonds, to form a pouch. The envelope web 50 can comprise a number of materials including nonwoven webs, paper webs, or webs of absorbent materials such as tissue paper. The envelope web 50 preferably comprises a nonwoven web similar to the webs used to form the topsheet 38. The nonwoven web is preferably hydrophilic to allow liquids to rapidly pass through the envelope web 50. Similar layered absorbent members (laminates) are more fully described in U.S. Pat. No. 4,578,068 (Kramer et al), issued Mar. 25, 1986.

Alternatively, the absorbent cores 42 of the present invention can consist solely of one or more (a plurality of the) porous, absorbent macrostructures of the present invention; can comprise a combination of layers including the macrostructures of the present invention; or any other absorbent core configurations including one or more of the macrostructures of the present invention.

Figure 5:
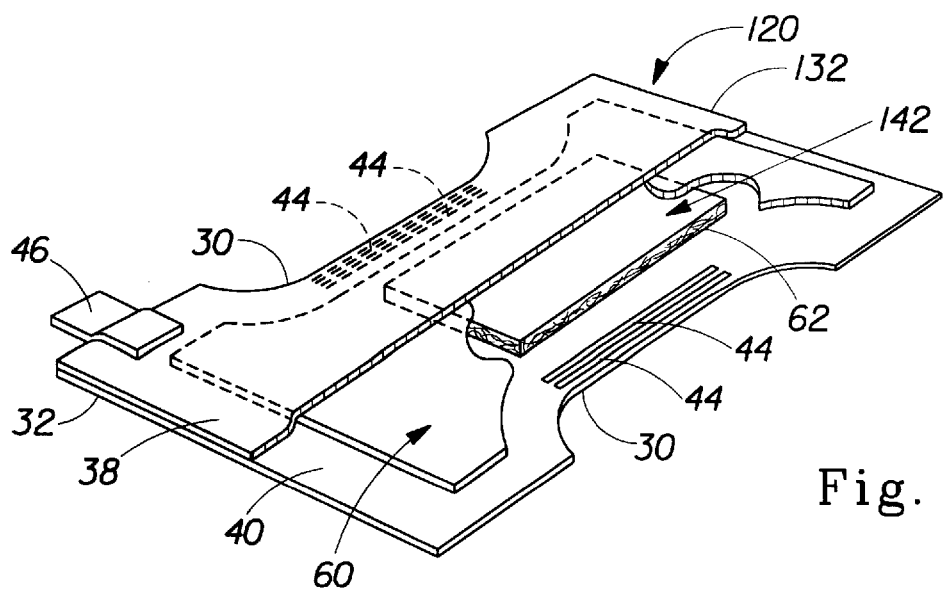
FIG. 5 is a perspective view of a disposable diaper embodiment according to the present invention wherein portions of the topsheet have been cut away to more clearly show an alternative dual-layer absorbent core embodiment.

FIG. 5 shows an alternative embodiment of the diaper 120 comprising a dual-layer absorbent core 142 comprising a modified hourglass-shaped absorbent member 60 and a sheet 62 of the porous, absorbent macrostructure positioned subjacent the absorbent member 60 (i.e., between the absorbent member 60 and the backsheet 40).

The absorbent member 60 serves to quickly collect and temporarily hold discharged liquids and to transport such liquids by wicking from the point of initial contact to other parts of the absorbent member 60 and to the macrostructure sheet 62. The absorbent member 60 preferably comprises a web or batt of fiber materials. Various types of fiber material can be used in the absorbent member 60 such as the fiber materials previously discussed herein. Cellulosic fibers are generally preferred for use herein, wood pulp fibers being especially preferred. The absorbent member 60 can also contain specific amounts of a particulate, absorbent, polymeric composition. The absorbent member 60, for example, can contain up to about 50% by its weight of the polymeric composition. In the more preferred embodiments, the absorbent member 60 contains from 0% to about 8% by its weight of a particulate, absorbent, polymeric composition. In alternatively preferred embodiments, the absorbent member 60 comprises chemically stiffened cellulosic fibers as previously discussed herein. Exemplary embodiments of the absorbent member 60 useful in the present invention are described in U.S. Pat. No. 4,673,402 (Weisman et al), issued Jun. 16, 1987; and U.S. Pat. No. 4,834,735 (Alemany et al), issued May 30, 1989. Absorbent members having a storage zone and an acquisition zone having a lower average density and a lower average basis weight per unit area than the storage zone so that the acquisition zone can effectively and efficiently rapidly acquire discharged liquid are especially preferred for use herein.

The absorbent member 60 can be of any desired shape, for example, rectangular, oval, oblong, asymmetric or hourglass-shaped. The shape of the absorbent member 60 can define the general shape of the resulting diaper 120. In the preferred embodiments as shown in FIG. 5, the absorbent member 60 is hourglass-shaped.

The macrostructure sheet 62 of the present invention need not be the same size as the absorbent member 60 and can, in fact, have a top surface which is substantially smaller or larger than the top surface area of the absorbent member 60. As shown in FIG. 5, the macrostructure sheet 62 is smaller than the absorbent member 60 and has a top surface area from about 0.10 to about 1.0 times that of the absorbent member 60. More preferably, the top surface area of the macrostructure sheet 62 will be only from about 0.10 to about 0.75, and more preferably from about 0.10 to about 0.5 times that of the absorbent member 60. In an alternative embodiment, the absorbent member 60 is smaller than the macrostructure sheet 62 and has a top surface area from about 0.25 to about 1.0 times, more preferably from about 0.3 to about 0.95 times that of the macrostructure sheet 62. In this alternative embodiment, the absorbent member 60 preferably comprises chemically stiffened cellulosic fibers, as previously described.

The macrostructure sheet 62 is preferably placed in a specific positional relationship with respect to the backsheet 40 and/or the absorbent member 60 in the diaper. More particularly, the macrostructure sheet 62 is positioned generally toward the front of the diaper so that the macrostructure sheet 62 is more effectively located to acquire and hold discharged liquids.

In alternatively preferred embodiments, a plurality of macrostructures, preferably from two to six macrostructure strips or sheets, can be substituted for the single macrostructure sheet 62 shown in FIG. 5. Further, additional absorbent layers, members, or structures can be placed into the absorbent core 142. For example, an additional absorbent member can be positioned between the macrostructure sheet 62 and the backsheet 40 to provide reserve capacity for the absorbent core 142 and/or a layer to distribute liquids passing through the macrostructure sheet 62 to other portions of the absorbent core 142 or to the macrostructure sheet 62. The macrostructure sheet 62 can also alternatively be positioned over the absorbent member 60 so as to be positioned between the topsheet 38 and the absorbent member 60.

Figure 6:
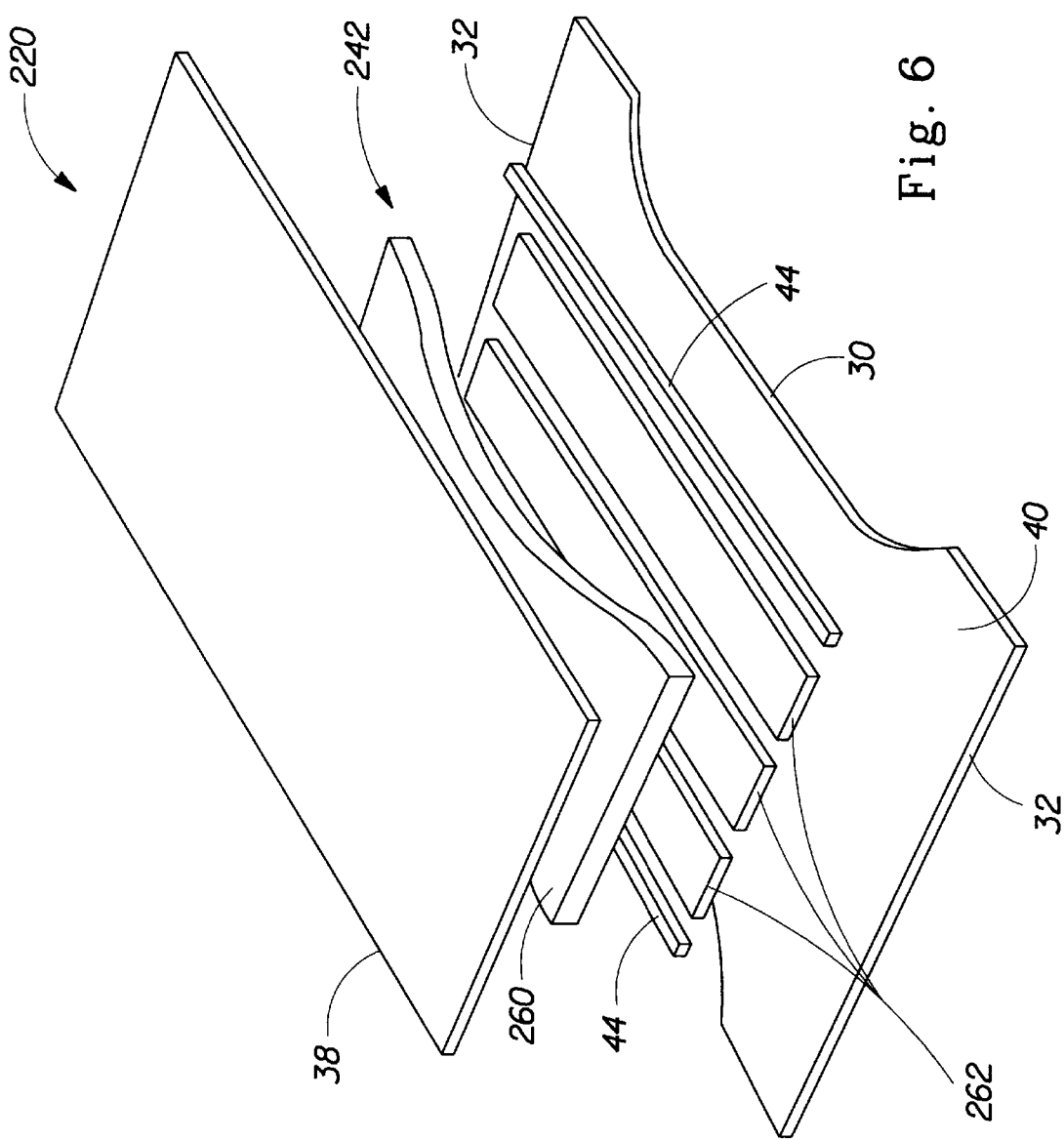
FIG. 6 is a blown-apart view of the components of a diaper structure, one of the components being an afternative dual-layer absorbent core where the absorbent macrostructure is in the form of a plurality of strips.

FIG. 6 shows an alternative embodiment of a diaper 220 comprising an alternative dual-layer absorbent core 242 comprising a rectangular shaped absorbent member 260 and three elongated parallel spaced macrostructure strips 262 positioned between absorbent member 260 and backsheet 40.

The absorbent member 260 serves to quickly collect and temporarily hold discharged liquids and to transport such liquids by wicking from the point of initial contact to other parts of the absorbent member 260 and to macrostructure strips 262. This absorbent member 260 preferably comprises a web or bat of fiber materials, more preferably chemically stiffened cellulosic fibers as previously discussed herein. Macrostructure strips 262 together act to acquire and hold the discharged liquids. By spacing macrostructure strips 262 from one another, a more effective surface area is presented for acquiring and holding the discharge liquids. This is particularly true since the spaced macrostructure strips 262 can swell and expand in the direction of their width, without interfering with the ability of adjacent strips to acquire discharged liquids.

In use, the diaper 20 is applied to a wearer by positioning the back waistband region under the wearer's back, and drawing the reminder of the diaper 20 between the wearers legs so that the front waistband region is positioned across the front of the wearer. The tape-tab fasteners 46 are then secured preferably to outwardly facing areas of the diaper 20. In use, disposable diapers or other absorbent articles incorporating the porous, absorbent macrostructures of the present invention tend to more quickly and efficiently distribute and store liquids and to remain dry due to the high absorbent capacity of the macrostructures. Disposable diapers incorporating the macrostructures of the present invention can also be thinner and more flexible.

The absorbent macrostructure of the present invention may also be used in an absorbent article such as that set forth in U.S. patent application Ser. No. 081621,030, filed Mar. 22, 1996. Specifically, an absorbent article comprising a fluid pervious topsheet, a backsheet and an absorbent core positioned between the topsheet and the backsheet. The absorbent core comprises at least one upper fluid storage component capable of expanding in the z-direction when contacted with aqueous body fluids to form a fluid acquisition zone, the upper fluid storage component being in direct fluid communication with the topsheet; the upper fluid storage component further comprising the absorbent macrostructure of the present invention. The absorbent core further comprises a fluid acquisition zone capable of receiving aqueous body fluids, the fluid acquisition zone being at least partially surrounded by the upper fluid storage component and positioned at least partially beneath the fluid discharge region of the absorbent core. The absorbent core further comprising a fluid acquisition/distribution component capable of acquiring and transporting aqueous body fluids, at least a portion of this fluid acquisition/distribution component being positioned underneath and in fluid communication with the upper fluid storage component, and at least a portion of the fluid acquisition/distribution component being positioned underneath the fluid acquisition zone.

IV. Absorbent Article Performance

With respect to absorbent articles comprising the absorbent macrostructures of the present invention, Applicants have discovered the ability to overcome the inverse relationship between fluid loading level (g or ml of fluid) and fluid acquisition rate (ml/sec) which has been generally accepted as the norm for absorbent articles. Thus, in one aspect, the present invention relates to an absorbent article that, in addition to being relatively thin, exhibits the ability to maintain the rate of fluid acquisition for each of two successive fluid loads. In another aspect, the invention relates to an absorbent article that exhibits the ability to increase the rate of fluid acquisition for each of two successive fluid loads. Preferably, the articles will exhibit maintained or increased fluid acquisition rates for each of three successive fluid loads, more preferably for each of four successive fluid loads.

The ability of an absorbent article to meet this criteria is measured as described in detail in the Test Method section, below, using an Acquisition Test. Briefly, fluid acquisition rates for a given absorbent article are determined for each of four successive loads of 50 ml per load, each load being delivered at a constant rate of about 10 ml/sec) of synthetic urine, with a 5 minute equilibration period between each load. The articles of the present invention exhibit maintained or increased fluid acquisition rates as the number of loads increases.

With respect to those articles that exhibit maintained fluid acquisition rates for at least two successive loads, it is required that these articles (including topsheet, backsheet and absorbent core; but excluding tape, leg cuffs, or other optional components) have a thickness, in the dry state, of no more than about 0.5 inches, preferably no more than about 0.25 inches, more preferably no more than about 0.2 inches. Thickness of the articles is measured with no pressure applied. While not a requirement, with regard to those articles of the present invention that exhibit increased fluid acquisition rates for at least two, three or four successive loads, it is preferred that these absorbent articles also satisfy the above thickness requirements.

In addition to exhibiting maintained/increased acquisition rates for successive fluid loads, preferred absorbent articles acquire fluid at a rate of at least about 2 ml/sec for the first 50 ml load, more preferably at least about 5 ml/sec. Though this is not a criteria that must be satisfied by these articles, meeting this criteria will more likely result in an article that is useful for the intended purpose.

V. Test Methods

A. Absorptive Capacity

The Absorptive Capacity of the absorbent particles is determined according to the Absorptive Capacity test described at Columns 27–28 of U.S. Pat. No. 5,124,188 (Roe et al), issued Jun. 23, 1992. In this test, the absorbent particles are placed within a "tea bag", immersed in an excess of Synthetic Urine for a specified period of time, and then centrifuged for a specific period of time. The ratio of absorbent particles final weight after centrifuging minus initial weight (net fluid gain) to initial weight determines the Absorptive Capacity.

B. Saline Flow Conductivity (SFC)

The Saline Flow Conductivity (SFC) of the precursor absorbent particles is determined according to the test procedure described in copending U.S. application Ser. No. 219,574 (Goldman et al), filed Mar. 29, 1994. In this test, a gel layer is formed from absorbent particles swollen in Jayco synthetic urine under a confining pressure. This test assesses the ability of the hydrogel layer formed from these absorbent particles to acquire and distribute body fluids when the particles are present at high concentrations and exposed to usage mechanical pressures. Darcy's law and steady-state flow methods are used for determining saline flow conductivity. (See, for example, "ABSORBENCY," ed. by P. K. Chatterjee, Elsevier, 1985, Pages 42–43 and "CHEMICAL ENGINEERING VOL. II, Third Edition, J. M. Coulson and J. F. Richardson, Pergamon Press, 1978, Pages 125–127.) The test fluid for the SFC test is Jayco synthetic urine.

C. Performance Under Pressure (PUP) Capacity

The Performance Under Pressure (PUP) Capacity of the precursor absorbent particles is determined according to the test procedure described in copending U.S. application Ser. No. 219,574 (Goldman et al), filed Mar. 29, 1994. This test determines the 60 minute gram/gram absorption of synthetic urine for absorbent particles that is laterally confined in a piston/cylinder assembly under a confining pressure of 0.7 psi (about 5 kPa). This test assesses the ability of absorbent particle layer to absorb body fluids, over a practical period of time, when the particles are present at high basis weight and high concentrations and exposed to usage pressures. These usage pressures include mechanical pressures resulting from the weight and/or motions of the wearer, mechanical pressures resulting from elastics and fastening systems, and the hydrostatic suction resulting from adjacent capillary (e.g., fibrous) layers and/or structures as they are drained of fluid. The test fluid for the PUP capacity test is Jayco synthetic urine. This fluid is absorbed by the absorbent particles under demand absorption conditions at near-zero hydrostatic pressure.

D. Demand Absorbency Capacity

The Demand Absorbency Capacity of the absorbent macrostructure is designed to measure the 60 minute gram/gram absorption of synthetic urine for absorbent structures that are under a pressure of 1.4 psi (about 10 kPa) at the beginning of the test (dry state) and 0.7 psi (about 5 kPa) at the end of the test (wet, swollen state). This test assesses the ability of an absorbent structure to absorb body fluids, over a practical period of time, when the absorbent structures are present at high basis weight and high concentrations and exposed to usage pressures. . These usage pressures include mechanical pressures resulting from the weight and/or motions of the wearer, mechanical pressures resulting from elastics and fastening systems, and the hydrostatic suction resulting from adjacent capillary (e.g., fibrous) layers and/or structures as they are drained of fluid. The test fluid for the Demand Absorbency Capacity test is Jayco synthetic urine. This fluid is absorbed by the absorbent structure under demand absorption conditions.

The following describes the Demand Absorbency Capacity measurement. The sample cell is a square shaped piston/cylinder assembly, and has a mesh bottom of 10 cm×10 cm in dimension. Absorbent structures (with and without fibers) are sampled into a dimension of 3.7 cm by 3.7 cm, and placed under 1.4 psi piston. As the sample is brought in contact with Jayco synthetic urine, it starts to imbibe Jayco synthetic urine. The change of weight is monitored and recorded continuously for the next 60 minutes. As a result, the dimension of the sample is increased by about 100%, as placed under a constant 1.4 psi external pressure.

E. Acquisition Test

This test simulates the introduction of urine into a diaper under the following conditions:

1) A pressure of 0.4 psi (about 28 g/cm$^2$) is applied to a diaper sample.
2) A total of 2 or more loadings of synthetic urine at a rate of 10 ml/sec are applied to the diaper sample, with a 5 minute time period (equilibration time) between each loading.

The following apparatus is employed:

| | |
|---|---|
| Conditioned room: | Temperature are humidity controlled within the following limits:<br>Temperature: 73 ± 2° F.<br>Relative Humidity: 50 ± 2% |
| Aquisition Tester: | Obtain from Concord-Renn Co., 6315 Warrick St., Cincinnati, Ohio, 452227, U.S.A.<br>Part<br><br>Test Bed (PLEXIGLAS)<br>Foam Base - 6" × 20" × 1" foam covered withpolyethylene backsheet material - foam type: Density 1.0 lb/ft$^3$<br>ODL 24 psi<br>Nozzle<br>Cover plate |
| Graduated cylinders:<br>(100 ml) (1,000 ml) | VWR Scientific, (100 ml) Catalog number: 24711-310 (1,000 ml) Catalog number: 24711-364 or equivalent |
| Erlenmeyer flask:<br>or (6,000 ml) | VWR Scientific Catalog number: 29135-307 equivalent |
| Digital pump: | Cole-Parmer Instrument Co., Tel. No. (800) 323-4340, U.S.A., Catalog number: G-075323-20 |
| Easy Load Pump Head: | Cole-Parmer INstrument Co. Catalog number: G-07518-02 |
| Distilled water: | convienient source |
| Dry Synthetic Urine: | Jayco SynUrine |

V. Specific Illustrations of Preparation of Macrostructures According to Present Invention The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

This example shows how to manufacture an absorbent macrostructure of the present invention.

The absorbent macrostructure is fabricated on a shuttle table by first laying down superabsorbent polymer particulate on a cellulose web, and subsequently spraying with an aqueous solution containing KYMENE. The shuttle table is designed to move back and forth for continuous laydown of superabsorbent polymer particulate, and has a speed range of 3 meters/min to 30 meters/min. The shuttle table is equipped with a fixed automatic powder feeder system for superabsorbent polymer particulates with the range of flow rate between 100 to 1000 grams per minute, and fixed automatic solution spray systems of spray rates ranging between 40 and 200 grams per minute. A typical operation condition includes a shuttle speed at 10 meter per minute, a feeding rate of the superabsorbent polymer particulates at 212 grams per minute, and a solution spray rate at 76 grams per minute.

Two different superabsorbent polymer particulates are used in this example. Both are crosslinked sodium polyacrylate. The first superabsorbent polymer is supplied by Nippon Shokubai under the trade name of AQUALIC CA-L76, and has a high PUP and medium gel volume. The second crosslinked sodium polyacrylate is IM-1000 supplied by Sanyo Chemical Industry, and has a low PUP and high gel volume. The cellulose web is a tissue towel available under the trade name of BOUNTY, which has 20 gm per meter square of basis weight. KYMENE is supplied by Hercules company under the trade name of KYMENE-PLUS, which contains 30% of polymer resin. Blending of at least two types of superabsorbent polymer particulate is carried out in a food mixer. The spray solution contains 10% by weight of KYMENE polymer resin, 45% of glycerol, and 45% of water. An additional polyethylacrylate-based latex polymer, supplied by Hoechst Gosei Co. under the trade name of MOWINYL-963, is included into the above solution at a level of 10%. The presence of a polyethylacrylate-based latex polymer is added to increase the softness and flexibility of the macrostructure.

The resulting macrostructure contains 77% superabsorbent polymer, 19% of solution and 4% cellulosic tissue towel. The total basis weight of the macrostructure is 480 grams per square meter, which is including 370 grams of superabsorbent polymer, 90 grams of sprayed solution, and 20 grams of BOUNTY towel. The weight ratio of the two types of superabsorbent polymers ranges from 0% to 100%.

EXAMPLE 2

This example shows how to manufacture an absorbent macrostructure of the present invention.

The absorbent macrostructure is produced by following the procedure set forth in Example 1, except the structure is made by attaching the AQUALIC CA-L76 superabsorbent polymer on one side of the tissue web, and the IM-1000 superabsorbent polymer on the other side of the web.

The resulting macrostructure contains 77% superabsorbent polymer, 19% of solution and 4% cellulosic tissue towel. The total basis weight of the macrostructure is 480 grams per square meter, which is including 370 grams of superabsorbent polymer, 90 grams of sprayed solution, and 20 grams of BOUNTY towel. The weight ratio of the two types of superabsorbent polymers ranges from 0% to 100%.

EXAMPLE 3

This example shows how to manufacture a baby diaper containing an absorbent macrostructure of the present invention.

The absorbent macrostructure of Example 1 is sampled into a diaper core dimension, and applied with a fluid impermeable backsheet film, wood fiber acquisition layer and a nonwoven topsheet, thereby forming a baby diaper.

The resulting diaper has a very low caliper due to the high concentration of superabsorbent polymer: 70% in weight as compared to a typical baby diaper cores containing about 40% superabsorbent polymers.

EXAMPLE 5

This example shows the manufacture of a diaper comprising a superabsorbent macrostructure of the present invention.

The superabsorbent macrostructure is prepared following the process of Example 1, except the concentration of superabsorbent polymer is increased to 90% by increasing the basis weight of the superabsorbent polymer to equal or greater than 1550 gram per square meter. The macrostructure is then slitted and stretched to form a net shaped core. The core is then applied with a fluid impermeable backsheet film a wood fiber acquisition layer and a nonwoven topsheet to make a baby diaper. The diaper has a very low caliper, as compared to conventional baby diapers, due to the high concentration of superabsorbent polymer in the core.

EXAMPLE 6

This example shows that employing a cationic aminoepichlorohydrin adduct, such as KYMENE, in the absorbent macrostructure of the present invention surprisingly enhances the Demand Absorbancy Capacity of the macrostructure.

Figure 7:
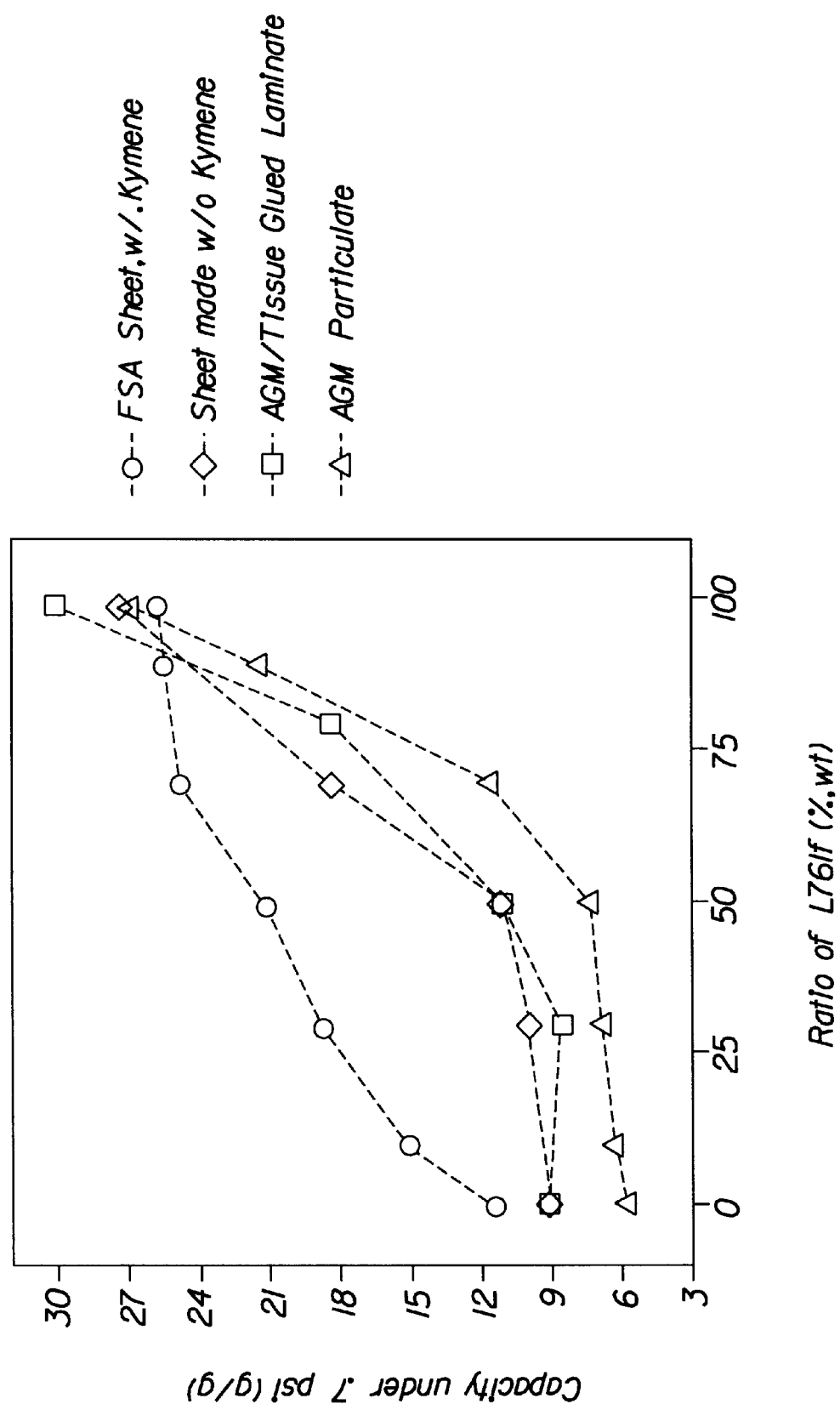
FIG. 7 is a profile of the Demand Absorbency Capacity of various macrostructures vs. weight percent of high PUP, L-76 superabsorbent polymer in different macrostructures.

FIG. 7 illustrates a comparison of Demand Absorbency Capacity of the absorbent macrostructure of the present invention, as compared to three different samples. Specifically, curve "---○---" illustrates the surprising effect of KYMENE to dramatically increase the under pressure demand absorbency capacity at the whole range of mixing ratios of two different superabsorbent polymers. This is compared to a similar structure prepared without using KYMENE (Curve "---◆---"), of which the 0.7 psi demand absorbency capacities increase stepwise only at the increase of the weight percent of high PUP superabsorbent particulates (L-76). Curve "---◆---" is also identical to curve "---Δ---", which is the test result of a layer of mixed superabsorbent particulates without KYMENE or glue additives. Another example of forming an absorbent structure without using KYMENE is by first sandwiching a layer of superabsorbent polymer particulates in between two ply of tissue, and gluing the tissue to form a laminate composite. This laminate structure (curve "---⊞---") does not show an extraordinary relationship (as seen in curve "---○---") between the under pressure demand absorbency capacity and the mixing ratio of superabsorbent polymers.

All publications, patent applications, and issued patents mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A porous, absorbent macrostructure having improved fluid handling capability and comprising an interparticle bonded aggregate comprising a multiplicity of interconnected crosslinked particles comprising substantially water-insoluble, absorbent, hydrogel-forming polymer material; the hydrogel-forming polymer material comprising a mixture selected from the group consisting of:

(a) mixtures of from about 50 to about 95% of a first hydrogel-forming polymer having a Saline Flow Conductivity (SFC) value of at least about $5 \times 10^{-7}$ $cm^3$ sec/g and a Performance under Pressure (PUP) capacity value of at least about 23 g/g under a confining pressure of 0.7 psi (5 kPa) and from about 5 to about 50% of a second hydrogel-forming polymer having an Absorptive Capacity value of at least about 25 g/g, (b) mixtures of from about 20 to about 40% of a first hydrogel-forming polymer in the form of spherical shaped particles and from about 60 to about 80% of a second hydrogel-forming polymer in the form of non-spherical shaped particles, and (c) combinations of (a) and (b);

the interparticle bonded aggregate having pores between adjacent particles, the pores being interconnected by intercommunicating channels so as to form a liquid permeable macrostructure, the circumscribed dry volume of the macrostructure being greater than about 0.008 mm$^3$.

2. The porous, absorbent macrostructure of claim 1 wherein the hydrogel-forming polymer material comprises a mixture of from about 20 to about 40% of a first hydrogel-forming polymer in the form of spherical shaped particles; and from about 60 to about 80% of a second hydrogel-forming polymer in the form of nonspherical shaped particles.

3. The porous, absorbent macrostructure of claim 1 wherein the hydrogel-forming polymer material comprises a mixture of from about 50 to about 95% of a first hydrogel-forming polymer having a Saline Flow Conductivity (SFC) value of at least about 5×10$^{-7}$ cm$^3$ sec/g and a Performance under Pressure (PUP) capacity value of at least about 23 g/g under a confining pressure of 0.7 psi (5 kPa) and from about 5 to about 50% of a second hydrogel-forming polymer having an Absorptive Capacity value of at least about 25 g/g.

4. The absorbent macrostructure of claim 1 wherein the particles are crosslinked at the surface thereof with a cationic amino-epichlorohydrin adduct.

5. The absorbent macrostructure of claim 1 further comprising a plasticizer.

6. The absorbent macrostructure of claim 1 further comprising a latex material.

7. An absorbent article comprising a liquid pervious topsheet; a liquid impervious backsheet joined with the topsheet; and an absorbent core positioned between the topsheet and the backsheet, the absorbent core comprising one or more of the macrostructures of claim 1.

8. The absorbent article of claim 7 wherein the absorbent core further comprises an absorbent member positioned between the topsheet and the macrostructure, the absorbent core comprising chemically stiffened cellulosic fibers.

9. The absorbent article of claim 7 wherein the article is a diaper.

10. A flexible, porous, absorbent sheet comprising an interparticle bonded aggregate comprising a multiplicity of interconnected crosslinked particles comprising substantially water-insoluble, absorbent, hydrogel-forming polymer material; the hydrogel-forming polymer material comprising a mixture selected from the group consisting of (a) mixtures of from about 50 to about 95% of a first hydrogel-forming polymer having a Saline Flow Conductivity (SFC) value of at least about 5×10$^{-7}$ cm$^3$ sec/g and a Performance under Pressure (PUP) capacity value of at least about 23 g/g under a confining pressure of 0.7 psi (5 kPa) and from about 5 to about 50% of a second hydrogel-forming polymer having an Absorptive Capacity value of at least about 25 g/g, (b) mixtures of from about 20 to about 40% of a first hydrogel-forming polymer in the form of spherical shaped particles and from about 60 to about 80% of a second hydrogel-forming polymer in the form of nonspherical shaped particles, and (c) combinations of (i) and (ii);

the interparticle bonded aggregate having pores between adjacent particles, the pores being interconnected by intercommunicating channels so as to form a liquid permeable macrostructure, the circumscribed dry volume of the macrostructure being greater than about 0.008 mm$^3$.

* * * * *

UNITED STATES PATENT AND TRADEMARK OFFICE
CERTIFICATE OF CORRECTION

PATENT NO. : 6,224,961 B1
DATED : May 1, 2001
INVENTOR(S) : Kesyin F. Hsueh et al.

It is certified that error appears in the above-identified patent and that said Letters Patent is hereby corrected as shown below:

Column 1,
Line 39, delete "Harnon" and insert -- Harmon --.

Column 5,
Line 6, delete "aftemative" and insert -- alternative --.

Column 9,
Line 36, delete "polyquatemary" and insert -- polyquaternary --.
Line 48, delete "hidrogel-forming" and insert -- hydrogel-forming --.

Column 10,
Line 10, delete "wo90108789" and insert -- wo90/08789 --.
Line 18, delete "L76If" and insert -- L76lf --.

Column 12,
Line 1, delete "L76If" and insert -- L76lf --.

Column 13,
Line 4, delete "piperazinei" and insert -- piperazine, --.

Column 20,
Line 48, delete " partides" and insert -- particles --.

Column 21,
Line 27, delete "quatemary" and insert -- quaternary --.

Column 24,
Line 51, delete "Altematively" and insert -- Alternatively --.

Column 27,
Line 36, delete "wearers" and insert -- wearer's --.
Line 49, delete "081621,030," and insert -- 08/621,030, --.

UNITED STATES PATENT AND TRADEMARK OFFICE
CERTIFICATE OF CORRECTION

PATENT NO. : 6,224,961 B1
DATED : May 1, 2001
INVENTOR(S) : Kesyin F. Hsueh et al.

It is certified that error appears in the above-identified patent and that said Letters Patent is hereby corrected as shown below:

Column 30,
Line 14, delete "are" and insert -- and --.
Line 23, delete "ODL" and insert -- IDL --.
Line 32, delete "INstrument" and insert -- Instrument --.
Line 34, delete "convienient" and insert -- convenient --.

Signed and Sealed this

Twenty-eighth Day of February, 2006

JON W. DUDAS
*Director of the United States Patent and Trademark Office*